US009637752B2

(12) United States Patent
Flasinski et al.

(10) Patent No.: US 9,637,752 B2
(45) Date of Patent: May 2, 2017

(54) PLANT REGULATORY ELEMENTS AND USES THEREOF

(71) Applicant: Monsanto Technology LLC, St. Louis, MO (US)

(72) Inventors: Stanislaw Flasinski, Chesterfield, MO (US); Charles R. Dietrich, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 365 days.

(21) Appl. No.: 14/026,946

(22) Filed: Sep. 13, 2013

(65) Prior Publication Data

US 2014/0109261 A1    Apr. 17, 2014

Related U.S. Application Data

(62) Division of application No. 12/935,272, filed as application No. PCT/US2009/038812 on Mar. 30, 2009, now Pat. No. 8,580,942.

(60) Provisional application No. 61/042,957, filed on Apr. 7, 2008.

(51) Int. Cl.
*C12N 15/82* (2006.01)
*C12N 15/113* (2010.01)

(52) U.S. Cl.
CPC ........ *C12N 15/8222* (2013.01); *C12N 15/113* (2013.01); *C12N 15/8225* (2013.01); *C12N 15/8227* (2013.01)

(58) Field of Classification Search
None
See application file for complete search history.

(56) References Cited

U.S. PATENT DOCUMENTS

| | | | |
|---|---|---|---|
| 6,018,099 A | 1/2000 | de Framond | |
| 6,759,529 B1 | 7/2004 | Misra | |
| 7,491,813 B2 | 2/2009 | Wu et al. | |
| 2007/0130644 A1 | 6/2007 | Hajdukiewicz et al. | |
| 2007/0130645 A1 | 6/2007 | Wei et al. | |
| 2009/0064374 A1* | 3/2009 | Duwenig ........... | C12N 15/8234 800/295 |
| 2011/0107468 A1 | 5/2011 | Flasinski et al. | |

FOREIGN PATENT DOCUMENTS

| | | |
|---|---|---|
| CN | 101063139 A | 10/2007 |
| WO | WO 95/23230 A1 | 8/1995 |
| WO | WO 01/98480 A2 | 12/2001 |
| WO | WO 03/000898 | 1/2003 |
| WO | WO 2004/106530 A1 | 12/2004 |
| WO | WO 2005/063997 A2 | 7/2005 |
| WO | WO 2005/063998 A2 | 7/2005 |
| WO | WO 2006/066168 A2 | 6/2006 |
| WO | WO 2009/126470 | 10/2009 |

OTHER PUBLICATIONS

Ludevid et al. The expression pattern of the tonoplast intrinsic protein γ-TIP in Arabidopsis thaliana is correlated with cell enlargement. Plant Physiology. 1992. 100: 1633-1639.*
Devos et al. Comparative genetic maps of foxtail millet (*Setaria italica*) and rice (*Oryza sativa*). Theoretical Applied Genetics. 1998. 96: 63-68.*
Chaumont et al. Characterization of a maize tonoplast aquaporin expressed in zones of cell division and elongation. Plant Physiology. 1998. 117: 1143-1152.*
Kim et al. A 20 nucleotide upstream element is essential for the nopaline synthase (nos) promoter activity. Plant Molecular Biology. 1994. 24: 105-117.*
Benfey et al., "The CaMV 35S enhancer contains at least two domains which can confer different developmental and tissue-specific expression patterns", EMBO Journal, 8(8):2195-2202, 1989.
Boutrot et al., "The triticum aestivum non-specific lipid transfer protein (TaLtp) gene family: comparative promoter activity of six TaLtp genes in transgenic rice," *Planta*, 225:843-862, 2007.
Cho et al., "Regulation of Root Hair Initiation and Expansin Gene Expression in Arabidopsis", Plant Cell, 14:3237-3253, 2002.
EMBL Accession No. CD725584, dated Jul. 14, 2007.
GenBank Accession No. AC243215, dated Nov. 20, 2010.
GenBank Accession No. AC243216, dated Nov. 20, 2010.
GenBank Accession No. AC243239, dated Nov. 20, 2010.
GenBank Accession No. AC243258, dated Nov. 20, 2010.
GenBank Accession No. AC243259, dated Nov. 20, 2010.
GenBank Accession No. AE015929, dated Mar. 5, 2010.
GenBank Accession No. AF269428, dated Dec. 6, 2001.
GenBank Accession No. AF270344, dated Aug. 1, 2000.
GenBank Accession No. AL606655, dated Apr. 16, 2005.
GenBank Accession No. AL713941, dated Jan. 16, 2006.
GenBank Accession No. AP005289, dated Feb. 16, 2008.
GenBank Accession No. CP000029, dated Mar. 5, 2010.
GenBank Accession No. EZ609827, dated May 25, 2010.
GenBank Accession No. GX558717, dated Dec. 13, 2010.
GenBank Accession No. GX564841, dated Dec. 13, 2010.
GenBank Accession No. GX652639, dated Dec. 13, 2010.
Hwang et al., "Aleurone- and embryo-specific expression of the β-glucuronidase gene controlled by the barley Chi26 and Ltp1 promoters in transgenic rice," Plant Cell Rep, 20(7):647-654, 2001.
Inokuma et al., "Transgenic Japanese lawngrass (*Zoysia japonica* Steud.) plants regenerated from protoplasts," *Plant Cell Reports*, 17:334-338, 1998.
Kothari et al., "Applications of biotechnology for improvement of millet crops: review of progress and future prospects," *Plant Biotechnology*, 22(2):81-88, 2005.
Lu et al., "The GUS reporter-aided analysis of the promoter activities of a rice metallothionein gene reveals different regulatory regions responsible for tissue-specific and inducible expression in transgenic Arabidopsis," *Transgenic Research*, 16:177-191, 2007.
Ludevid et al., "The expression pattern of the tonoplast intrinsic protein y-TIP in arabidopsis thaliana is correlated with cell enlargement," *Plant Physiol.*, 100:1633-1639, 1992.
NCBI Accession No. XM_001033261, dated May 7, 2009.
NCBI Accession No. XM_002192136, dated Feb. 25, 2009.

(Continued)

*Primary Examiner* — Ashley K Buran
(74) *Attorney, Agent, or Firm* — Dentons US LLP; Carine M. Doyle, Esq.

(57) ABSTRACT

The present invention provides novel regulatory elements for use in plants. The present invention also provides DNA constructs containing these novel regulatory elements; transgenic cells, plants, and seeds containing these novel regulatory elements; and methods for preparing and using the same.

9 Claims, 4 Drawing Sheets

(56) References Cited

OTHER PUBLICATIONS

Odell et al., "Identification of DNA sequences required for activity of the cauliflower mosaic virus 35S promoter", *Nature*, 313:810-812, 1985.

Piechulla et al., "Identification of tomato Lhc promoter regions necessary for circadian expression", *Plant Molecular Biology*, 38:655-662, 1998.

Ren et al., "Functional analysis of the rice metallothionein gene OsMT2b promoter in transgenic Arabidopsis plants and rice germinated embryos," *Plant Science*, 176:528-538, 2009.

Sreenivasulu et al., "Differential response of antioxidant compounds to salinity stress in salt-tolerant and salt-sensitive seedlings of foxtail millet (*Setaria italica*)," *Physiologia Plantarum*, 109:435-442, 2000.

Welsch et al., "Structural and functional characterization of the phytoene synthase promoter from *Arabidopsis thaliana*", *Planta*, 216:523-534, 2003.

Zhao et al., "Nucleotide sequence of ribulose-1, 5-biphosphate carboxylase/oxygenase large subunit gene from millet (set ar1a it alica)," *Acta Botanica Sinica*, 38(9):719-724, 1996.

Suzuki et al., "The pck1 promoter from *Urochloa panicoides* (a C4 plant) directs expression differently in rice (a C3 plant) and maize (a C4 plant)", *Plant Science*, 165(3):603-611, 2003.

Yin et al., "Cloning Methods of Plant Gene Promoters and Their Applications," *Molecular Plant Breeding*, 4(3S):85-91, 2006.

Kozaki et al., "The Promoter of the Gene for Plastidic Glutamine Synthetase (GS2) from Rice is Developmentally Regulated and Exhibits Substrate-Induced Expression in Transgenic Tobacco Plants," *Plant and Cell Physiology*, 33(3):233-238, 1992.

Samac et al., "A Comparison of Constitutive Promoters for Expression of Transgenes in Alfalfa (*Medicago sativa*)," *Transgenic Research*, 13(4):349-361, 2004.

\* cited by examiner 2062 nt ▬▬▬▬▬▬▬▬▬▬▬▬▬▬▬ SEQ ID NO: 15

1563 nt ▬▬▬▬▬▬▬▬▬▬▬ SEQ ID NO: 18

915 nt ▬▬▬▬▬ SEQ ID NO: 20

FIGURE 1

1516 nt ▮▮▮▮▮▮▮▮▮▮▮▮▮▮▮ SEQ ID NO: 8

483 nt ▮▮▮▮▮▮ SEQ ID NO: 5

FIGURE 2

```
SEQ ID NO:10   TGGTAAAATCAATTCATATGCTTATACTTCAAAAACCAATTTATGTGTATATACTTGGAA
SEQ ID NO:13   TGGTAAAATCAATTCATATGCTTATACTTCAAAAACCAATTTATGTGTATATACTTGGAA
               ************************************************************

SEQ ID NO:10   AAATTAGATTAAGTATTTCAATTTATTTGCTTATATTTCAAAAATAAATTCTTGTGCATA
SEQ ID NO:13   AAATTAGATTAAGTATTTCAATTTATTTGCTTATATTTCAAAAATAAATTCTTGTGCATA
               ************************************************************

SEQ ID NO:10   TACTTAGAAAAATTAGATTAAGTATTTCAATTTATTTGCTTATACTTCAAAAATCAATTC
SEQ ID NO:13   TACTTAGAAAAATTAGATTAAGTATTTCAATTTATTTGCTTATACTTCAAAAATCAATTC
               ************************************************************

SEQ ID NO:10   TTGTGTATATACTTACAAAAATTAGATTAAGTATTTCAATTTAATTGCTTATATTTGAAG
SEQ ID NO:13   TTGTGTACATACTTAGAAAAATTAGATTAAGTATTTCAATTTAATTGCTTATATTTGAAG
               ******* ******* ********************************************

SEQ ID NO:10   TAAGTCAATTGTGCAAACCCATTGATCTACTATATATGTAATAAACTTTGCCAATGACAC
SEQ ID NO:13   TAAGTCAATTGTGCAAACCCATTGATCTACTATATATGCAATAAACTTTGCCAATGACAC
               ************************************** *********************

SEQ ID NO:10   AGATGATGTACAGGAAAGATAGAATCTTCAAGTGGATTTCTTCTAGACGAGGTCATAAAT
SEQ ID NO:13   AGATGATGTACAGGAAAGATAGAATCTTCAAGTGGATTTCTTCTAGACGAGGTCATAAAT
               ************************************************************

SEQ ID NO:10   CCAGCGGGGGAGTTTCATAATGATGCATCAAATCTACAGCACCGTCAGGACTCGGGTTTA
SEQ ID NO:13   CCAGCGGGGGAGTTTCATAATGATGCATCAAATCTACAGCACCGTCAGGACTCGGGTTTA
               ************************************************************

SEQ ID NO:10   GAATAGTAGAAATGATATGTGTACGCACAATATGTCTATATATATGTATAATATTATTCA
SEQ ID NO:13   GAATAGTAGATATGATATGTGTACGCACAATATGTCTATATATATGTATAATATTATTCA
               ********** *************************************************

SEQ ID NO:10   TATATGTGTATGCATAATATGTATATATATAATAGTATCTTAAATGTAATATTGAAGATA
SEQ ID NO:13   TATATGTGTATGCATAATATGTATATATATAATAGTATCTTAAATGTAATATTGAAGATA
               ************************************************************

SEQ ID NO:10   AATAGAACTTTATATATATTAGCGTATTAGAAGTAGTATACGTATGAATATAGAATAAAG
SEQ ID NO:13   AATAGAACTTTATATATATTAGCGTATTAGAAGTAGTATACGTAAGAATATAGAATAAAG
               ******************************************** **************

SEQ ID NO:10   AAAAGAAAATAAGAAAAGAAAGGAAAAAAACAAATCAGTACCGGTCGGGGAGACCAACC
SEQ ID NO:13   AAAAG-AAAATAAGAAAAGAAAG-GAAAAAACAAATCAGTACCGGTTGGGGAGACCAACC
               ***** ***************** ********************** *************

SEQ ID NO:10   GGCACTAATTAGGCCCTTTAGTGCCCTCCCGCCACCCTCTCCTCCCTCTTCTCTCGCCGC
SEQ ID NO:13   GGCACTAATTAGGCCCTTTAGTGCCTTCCCGCCACCCTCTCCTCCCTCTTCTCTCGCCGC
               ************************* **********************************

SEQ ID NO:10   CCTCTCCTCCCTCTCAGCTCTTCCCGACCCCTTCCTCTCCCACTGCCGCCCCCTCCCTCT
SEQ ID NO:13   CCTCTCCTCCCTCTCAGCTCCTCCCGACCCCTTCCTCTCCCACTGTCGCCCCCTCCCTCT
               ******************** ************************ **************

SEQ ID NO:10   CTCCGCCGACCACCATCGTCCTGCGTGATCTCCCTCTCCTCACCCTCGGCTGCCCCTCCT
SEQ ID NO:13   CCCCGCCGACCACCATCGTCGTGCGTGATCTCCCTCTCCTCACCCTCGGCTGCCCCTCCT
               * ****************** ***************************************

SEQ ID NO:10   CT-CCCCCTTCGCTCACCCCTCACTCGTGGCAGTGAG---------------GAGCAG
SEQ ID NO:13   CTCCCCCCTTCGCTCACCCCTCACTCGTGGCAGTGAGGAGCGGCGGCGGGGTGAGAGCAG
               ** ********************************* ****

SEQ ID NO:10   CGGCAACACATAGATCCGGTGGTGGCAGTGCAGGTTCCAGTGAAGAAGGAGCTAGCACGG
SEQ ID NO:13   CGGCAACACATAGATCCGGTGGTGGCGGTGCAGGTTCCAGTGAAGAAGGAGCTAGCACGG
               ************************** *********************************

SEQ ID NO:10   ATCCGACGAAGAAGGAGCTGCTTGCGGTGGCGTAGGTGGGCGGCCCTGGCGGCGCGGCCT
SEQ ID NO:13   ATCCGACGAAGAAGGAGCTGGTTGCGGTGGCGTAGGTGGGCGGCCCTGGCGGCGCGGCCT
               ******************** ***************************************
```

FIGURE 3A

```
SEQ ID NO:10    CAGCTTCCTCTCCCCGTACGCCTCTCTCTCTCTCTCTATGAGCCGGATCCGGTAGGAC
SEQ ID NO:13    CAGCTTCCTCTCCCCGTACGCCTCTCTCTCTCT----ATGAGCCGGATCCGGTAGGAC
                *********************************    ********************

SEQ ID NO:10    CAAGGCAGTTGGCGGCTGGTGGGGCGGCAACGGCCAGATCCAGCGAGATGCGGCCGGTCG
SEQ ID NO:13    CAAGGCAGTTGGCGGCTGGTGGGGCGGCAACGGCCAGATCCAGCGAGATGCTGCCGGTCG
                *************************************************** *******

SEQ ID NO:10    GATCCGGCGAGGCAGCGCAAGGCCGGGGCGTAAGGCGGCCGGCAGCACCATTTTTTTGTT
SEQ ID NO:13    GATCCGGCGAGGCAGCGCAAGGCCGGGGCGTAAGGCGGCCGGCAGCACCATTTTTTTGTT
                ************************************************************

SEQ ID NO:10    TTTTTAATAGGCCTTCACCGCCAGTTCCAAAACCAGCGGTGATGGGGTATCCCCATCACT
SEQ ID NO:13    TTTTTAACAGGCCTTCACCGCCAGTTCCAAAACCAGCGGTGATGGGGTATCCCCATCACT
                ******* ****************************************************

SEQ ID NO:10    ACCGAAAGTCAGACGATGGATCCAAACCGACGGTGAAGACTGGTTTGGAGCCGGCAGTGA
SEQ ID NO:13    ACCGAAAGTCAGACGATGGATCCAAACCGACGGTGAAGACTGGTTTGGAGCCGGCAGTGA
                ************************************************************

SEQ ID NO:10    TGAACCTCTGGAGTAGTGCTTATGGCTGGGGGCATTGACATTCTTTTTACTAACTTTCTT
SEQ ID NO:13    TGAACCTCTGGAGTAGTGCTTATGGCTGGGGGCATTGACATTCTTTTTACTAACTTTCTT
                ************************************************************

SEQ ID NO:10    CCTACCACGTAGTATGCAATAATTGTACGTAATACTAGTAGCTGATGATAAGTTTGATAT
SEQ ID NO:13    CCTACCACGTAGTATGCAATAATTGTACGTAATACTAGTAGCTGATGATAAGTTTGATAT
                ************************************************************

SEQ ID NO:10    AAGACTATCAAGCGGTCTCGACATTTCACAATCTCGTGCAGCACATGGACAGCTATACTA
SEQ ID NO:13    AAGACTATCAAGCGGTCTCGACATTTCACAATCTCGTGCAACACATGGACAGCTATACTA
                **************************************** *******************

SEQ ID NO:10    ACGAGAAGTCGAGGACGACAGCCCACCGACTTGACAAATCTGTACAAAATATGCTAGAAA
SEQ ID NO:13    ACGAGAAGTCGAGAACGACAGCCCACCGACTTGACAAATCTGTACAAAATATGCTAGAAA
                ************* **********************************************

SEQ ID NO:10    AATATTGCACCAATCAAACATTGCCCATCAAGGCCACCAAGGATACATGATGACAACGGC
SEQ ID NO:13    AATATTGCACCAATCAAACATTGCCCATCAAGGCCACCAAGGATACATGATGACAACGGC
                ************************************************************

SEQ ID NO:10    CAATCAGACTTCAAAGATATCTCAACATCATACACACAGAAGGAAGAGATGATGACTCCA
SEQ ID NO:13    CAATCAGACTTCAAAGATATCTCAACATCATACACACAGAAGGAAGAGATGATGACTCCA
                ************************************************************

SEQ ID NO:10    GTTTAACTTTCATCGACGACTCCTATAAATACGACCCTCTTCCTGTACGCCTCCTCATTC
SEQ ID NO:13    GTTTAACTTTCATCGACGACTCCTATAAATACGACCCTCTTCCTGTACGCCTCCTCATTC
                ************************************************************

SEQ ID NO:10    CAAC
SEQ ID NO:13    CAAC
                ****
```

FIGURE 3B

PLANT REGULATORY ELEMENTS AND USES THEREOF

This application is a divisional of U.S. application Ser. No. 12/935,272, filed Dec. 14, 2010, which application is a 371 application of PCT/US2009/038812, filed Mar. 30, 2009, and claims the benefit of priority of U.S. provisional application No. 61/042,957, filed Apr. 7, 2008, each of the entire disclosures of which are herein incorporated by reference in their entireties.

INCORPORATION OF SEQUENCE LISTING

The sequence listing that is contained in the file named "MONS222WO_Sequence_Listing", which is 30.2 Kbytes (as measured in Microsoft Windows®) and was created on Mar. 30, 2009, is filed herewith by electronic submission and is incorporated by reference herein.

FIELD OF THE INVENTION

The invention relates to the field of plant molecular biology and plant genetic engineering and DNA molecules useful for modulating gene expression in plants.

BACKGROUND

Regulatory elements are genetic elements that regulate gene activity by modulating the transcription of an operably linked transcribable polynucleotide molecule. Such elements include promoters, leaders, introns, and 3' untranslated regions and are useful in the field of plant molecular biology and plant genetic engineering.

SUMMARY OF THE INVENTION

The present invention provides novel regulatory elements from Foxtail millet (*Setaria italica* (L.) Beauv) for use in plants. The present invention also provides DNA constructs comprising the regulatory elements. The present invention also provides transgenic plant cells, plants, and seeds comprising the regulatory elements operably linked to a transcribable polynucleotide molecule. The present invention also provides methods of making and using the regulatory elements, the DNA constructs comprising the regulatory elements, and the transgenic plant cells, plants, and seeds comprising the regulatory elements operably linked to a transcribable polynucleotide molecule.

BRIEF DESCRIPTION OF THE DRAWINGS

FIG. 1 illustrates the three promoter variants designed from the regulatory elements from the Lipid Transfer Protein gene. SEQ ID NO: 15 is P-SETit.Rcc3-1:1:1 and is 2062 nucleotide base pairs in length; SEQ ID NO: 20 is P-SETit.Rcc3-1:1:11 and is 915 nucleotide base pairs in length; and SEQ ID NO: 18 is P-SETit.Rcc3-1:1:10 and is 1563 nucleotide base pairs in length.

FIG. 2 illustrates the two promoter variants designed from the regulatory elements from the Metallothionein-like protein gene. SEQ ID NO: 5 is P-SETit.Mtha-1:1:1 and is 483 base pairs long; SEQ ID NO: 8 is P-SETit.Mthb-1:1:2 and is 1516 base pairs in length.

FIGS. 3A and 3B collectively illustrate a sequence alignment produced using CLUSTAL W (1.82) multiple sequence alignment of the two allelic variants of the promoters from the Dehydration Related Protein gene. In the consensus below the aligned sequences, matches are marked with "*", mismatches are marked with ".", and deletions/insertions are marked with "−". The two allelic variants had identical leader sequences, but the promoter sequences were sequence variants when aligned. SEQ ID NO: 10 is P-SETit.DRPa-1:1:1 and SEQ ID NO: 13 is P-SETit.DRPb-1:1:1.

DETAILED DESCRIPTION OF THE INVENTION

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e., a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein is that required by Title 37 of the United States Code of Federal Regulations §1.822 and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native or natural state. In one embodiment, the term "isolated" refers to a DNA molecule that is at least partially separated from the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated even when integrated into the chromosome of a host cell or present in a nucleic acid solution with other DNA molecules.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein, the term "sequence identity" refers to the extent to which two optimally aligned polynucleotide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided as SEQ ID NO: 1-20.

As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, provided herein as SEQ ID NO: 1-20, has about 85 percent identity or higher, about 90 percent identity or higher, about 95 percent identity or higher, or at least 96 percent identity, 97 percent identity, 98 percent identity, or 99 percent identity to the reference sequence and has gene regulatory activity.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. Gene regulatory activity may be positive and/or negative and the effect may be characterized by its temporal, spatial, developmental, tissue, environmental, physiological, pathological, cell cycle, and/or chemically responsive qualities as well as by quantitative or qualitative indications.

Regulatory elements such as promoters, leaders, introns, and transcription termination regions are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders, that function in plants are therefore useful for modifying plant phenotypes through the methods of genetic engineering.

Regulatory elements may be characterized by their expression pattern, i.e. as constitutive and/or by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked DNA molecule into a transcribed RNA molecule. Expression may be characterized by its temporal, spatial, developmental, tissue, environmental, physiological, pathological, cell cycle, and/or chemically responsive qualities as well as by quantitative or qualitative indications. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules. Promoters useful in practicing the present invention include SEQ ID NO: 2, 5, 8, 10, 13, and 20 or fragments or variants thereof.

In one embodiment, fragments are provided of a promoter sequence disclosed herein. Promoter fragments may exhibit promoter activity, and may be useful alone or in combination with other promoters and promoter fragments, such as in constructing chimeric promoters. In specific embodiments, fragments of a promoter are provided comprising at least about 50, 95, 150, 250, 500, or about 750 contiguous nucleotides of a polynucleotide molecule having promoter activity disclosed herein. Such fragments may exhibit at least about 85 percent, about 90 percent, about 95 percent, about 98 percent, or about 99 percent, or greater, identity with a reference sequence when optimally aligned to the reference sequence.

A promoter or promoter fragment may also be analyzed for the presence of known promoter elements, i.e. DNA sequence characteristics, such as a TATA-box and other known transcription factor binding site motifs. Identification of such known promoter elements may be used by one of skill in the art to design variants of the promoter having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box. A promoter may naturally comprise one or more enhancer elements that affect the transcription of an operably linked polynucleotide sequence. An isolated enhancer element may also be fused to a promoter to produce a chimeric promoter-.cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. Leaders useful in practicing the present invention include SEQ ID NO: 3, 6, 11, and 16 or fragments or variants thereof.

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is in composition similar, but not identical to, a first DNA molecule and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. In the present invention, a polynucleotide sequence provided as SEQ ID NO: 1-20 may be used to create variants that are in composition similar, but not identical to, the polynucleotide sequence of the original regulatory element, while still maintaining the general functionality, i.e. same or similar expression pattern, of the original regulatory element. Production of such variants of the present invention is well within the ordinary skill of the art in light of the disclosure and is encompassed within the scope of the present invention.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e., operably linked. As used herein, the term "vector" means any recombinant polynucleotide construct that may be used for the purpose of transformation, i.e., the introduction of heterologous DNA into a host cell.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell.

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404; however, other strains known to those skilled in the art of plant transformation can function in the present invention.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art, see, for example, *Molecular Cloning: A Laboratory Manual*, $3^{rd}$ edition Volumes 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011 in their entirety. These types of vectors have also been reviewed in the scientific literature (see, for example, Rodriguez, et al., *Vectors: A Survey of Molecular Cloning Vectors and Their Uses*, Butterworths, Boston, (1988) and Click, et al., *Methods in Plant Molecular Biology and Biotechnology*, CRC Press, Boca Raton, Fla. (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology*, 153: 253-277 (1987)). Other recombinant vectors useful for plant transformation, including the pCaMVCN transfer control vector, have also been described in the scientific literature (see, for example, Fromm, et al., *Proc. Natl. Acad. Sci. USA*, 82: 5824-5828 (1985)).

Various regulatory elements may be included in a construct. Any such regulatory elements may be provided in combination with other regulatory elements. Such combinations can be designed or modified to produce desirable regulatory features. Constructs of the present invention would typically comprise at least one regulatory element operably linked to a transcribable polynucleotide molecule operably linked to a 3' transcription termination molecule.

Constructs of the present invention may include any promoter or leader known in the art. For example, a promoter of the present invention may be operably linked to a heterologous non-translated 5' leader such as one derived from a heat shock protein gene (see, for example, U.S. Pat. No. 5,659,122 and U.S. Pat. No. 5,362,865). Alternatively, a leader of the present invention may be operably linked to a heterologous promoter such as the Cauliflower Mosaic Virus 35S transcript promoter (see, U.S. Pat. No. 5,352,605).

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain elements enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347).

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley, et al., *Proc. Natl. Acad. Sci. USA*, 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. No. 5,188,642 and U.S. Pat. No. 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.*, 210:437-442 (1987)) or the *Petunia hybrida* EPSPS CTP (CTP4) (See, della-Cioppa et al., *Proc. Natl. Acad. Sci. USA*, 83:6873-6877 (1986)) has been show to target heterologous EPSPS protein sequences to chloroplasts in transgenic plants (See, U.S. Pat. Nos. 5,627,061; 5,633,435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those having sequences useful for gene suppression. A "transgene" refers to a transcribable polynucleotide molecule heterologous to a host cell and/or a transcribable polynucleotide molecule artificially incorporated into a host cell's genome.

A promoter of the present invention may be operably linked to a transcribable polynucleotide molecule that is heterologous with respect to the promoter molecule. As used herein, the term "heterologous" refers to the combination of two or more polynucleotide molecules when such a combination would not normally be found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of an RNA transcript is desired. Such expression of an RNA transcript may result in translation of the resulting mRNA molecule and thus protein expression. Alternatively, a transcribable polynucleotide molecule may be designed to ultimately cause decreased expression of a specific gene or protein. This may be accomplished by using a transcribable polynucleotide molecule that is oriented in the antisense direction. One of ordinary skill in the art is familiar with using such antisense technology. Briefly, as the antisense transcribable polynucleotide molecule is transcribed, the RNA product hybridizes to and sequesters a complementary RNA molecule inside the cell. This duplex RNA molecule cannot be translated into a protein by the cell's translational machinery and is degraded in the cell. Any gene may be negatively regulated in this manner.

Thus, one embodiment of the invention is a regulatory element of the present invention, such as those provided as SEQ ID NO: 1-20, operably linked to a transcribable polynucleotide molecule so as to modulate transcription of the transcribable polynucleotide molecule at a desired level or in a desired pattern upon introduction of said construct into a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type provides a desirable characteristic associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a promoter of the present invention is incorporated into a construct such that the promoter is operably linked to a transcribable polynucleotide molecule that is a gene of agronomic interest. The expression of the gene of agronomic interest is desirable in order to confer an agronomically beneficial trait. A beneficial agronomic trait may be, for example, but not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. USRE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. USRE37,543; 6,228,623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding a RNA molecule that causes the targeted modulation of gene expression of an endogenous gene, for example via antisense (see, e.g., U.S. Pat. No. 5,107,065); inhibitory RNA ("RNAi", including modulation of gene expression via miRNA-, siRNA-, trans-acting siRNA-, and phased sRNA-mediated mechanisms, e.g., as described in published applications US 2006/0200878, US 2008/0066206, and US2009/0070898; or cosuppression-mediated mechanisms. The RNA could also be a catalytic RNA molecule (e.g., a ribozyme or a riboswitch; see e.g., US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US2007/0124836) and compositions isolated from nematode pests (U.S. Patent Publication No. US2007/0250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS described in U.S. Pat. No. 5,599,670), green fluorescent protein and variants thereof (GFP described in U.S. Pat. Nos. 5,491,084 and 6,146,826), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, dalapon, dicamba, cyclohexanedione, protoporphyrinogen oxidase inhibitors, and isoxaflutole herbicides. Transcribable polynucleotide molecules encoding proteins involved in herbicide tolerance are known in the art, and include, but are not limited to, a transcribable polynucleotide molecule encoding 5-enolpyruvylshikimate-3-phosphate synthase (EPSPS for glyphosate tolerance described in U.S. Pat. Nos. 5,627,061; 5,633,435; 6,040,497; and 5,094,945); a transcribable polynucleotide molecule encoding a glyphosate oxidoreductase and a glyphosate-N-acetyl transferase (GOX described in U.S. Pat. No. 5,463,175; GAT described in U.S. Patent publication No. 2003/0083480, and dicamba monooxygenase U.S. Patent publication No. 2003/0135879); a transcribable polynucleotide molecule encoding bromoxynil nitrilase (Bxn for Bromoxynil tolerance described in U.S. Pat. No. 4,810,648); a transcribable polynucleotide molecule encoding phytoene desaturase (crtI) described in Misawa, et al., *Plant Journal,* 4:833-840 (1993) and Misawa, et al., *Plant Journal,* 6:481-489 (1994) for norflurazon tolerance; a transcribable polynucleotide molecule encoding acetohydroxyacid synthase (AHAS, aka ALS) described in Sathasiivan, et al., *Nucl. Acids Res.,* 18:2188-2193 (1990) for tolerance to sulfonylurea herbicides; and the bar gene described in DeBlock, et al., *EMBO Journal,* 6:2513-2519 (1987) for glufosinate and bialaphos tolerance. The promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art and are encompassed by the present invention.

Cell Transformation

The invention is also directed to a method of producing transformed cells and plants which comprise a promoter operably linked to a transcribable polynucleotide molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.,* 42:205 (1991)).

Technology for introduction of a DNA molecule into cells is well known to those of skill in the art. Methods and materials for transforming plant cells by introducing a plant DNA construct into a plant genome in the practice of this invention can include any of the well-known and demonstrated methods including, but not limited to:

(1) chemical methods (Graham and Van der Eb, *Virology,* 54:536-539 (1973) and Zatloukal, et al., *Ann. N.Y. Acad. Sci.,* 660:136-153 (1992));

(2) physical methods such as microinjection (Capecchi, *Cell,* 22:479-488 (1980)), electroporation (Wong and Neumann, *Biochim. Biophys. Res. Commun.,* 107:584-587 (1982); Fromm, et al, *Proc. Natl. Acad. Sci. USA,* 82:5824-5828 (1985); U.S. Pat. No. 5,384,253) particle acceleration (Johnston and Tang, *Methods Cell Biol.,* 43(A):353-365 (1994); Fynan, et al., *Proc. Natl. Acad. Sci. USA,* 90:11478-11482 (1993)): and microprojectile bombardment (as illustrated in U.S. Pat. Nos. 5,015, 580; 5,550,318; 5,538,880; 6,160,208; 6,399,861; and 6,403,865);

(3) viral vectors (Clapp, *Clin. Perinatol.,* 20:155-168 (1993); Lu, et al., *J. Exp. Med.,* 178:2089-2096 (1993); Eglitis and Anderson, *Biotechniques,* 6:608-614 (1988));

(4) receptor-mediated mechanisms (Curiel et al., *Hum. Gen. Ther.,* 3:147-154 (1992) and Wagner, et al., *Proc. Natl. Acad. Sci. USA,* 89:6099-6103 (1992);

(5) bacterial mediated mechanisms such as *Agrobacterium*-mediated transformation (as illustrated in U.S. Pat. Nos. 5,824,877; 5,591,616; 5,981,840; and 6,384,301);

(6) direct introduction into pollen by injecting a plant's reproductive organs (Zhou, et al., *Methods in Enzymology*, 101:433, (1983); Hess, *Intern Rev. Cytol.*, 107:367 (1987); Luo, et al., *Plant Mol Biol. Reporter,* 6:165 (1988); Pena, et al., *Nature*, 325:274 (1987));

(7) protoplast transformation (as illustrated in U.S. Pat. No. 5,508,184); and (8) injection into immature embryos (Neuhaus, et al., *Theor. Appl. Genet.*, 75:30 (1987)).

Any of the above described methods may be utilized to transform a host cell with one or more promoters and/or constructs of the present. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Methods for transforming dicotyledonous plants, primarily by use of *Agrobacterium tumefaciens* and obtaining transgenic plants have been published for cotton (U.S. Pat. Nos. 5,004,863; 5,159,135; and 5,518,908); soybean (U.S. Pat. Nos. 5,569,834 and 5,416,011; see also, McCabe, et al., *Biotechnology,* 6:923 (1988) and Christou et al., *Plant Physiol.* 87:671-674 (1988)); *Brassica* (U.S. Pat. No. 5,463,174); peanut (Cheng et al., *Plant Cell Rep.*, 15:653-657 (1996) and McKently et al., *Plant Cell Rep.*, 14:699-703 (1995)); papaya; and pea (Grant et al., *Plant Cell Rep.*, 15:254-258 (1995)).

Transformations of monocotyledon plants using electroporation, particle bombardment, and *Agrobacterium* have also been reported. Transformation and plant regeneration have been achieved in asparagus (Bytebier, et al., *Proc. Natl. Acad. Sci. U.S.A.*, 84:5354 (1987); barley (Wan and Lemaux, *Plant Physiol,* 104:37 (1994)); maize (Rhodes, et al., *Science* 240:204 (1988), Gordon-Kamm, et al., *Plant Cell*, 2:603-618 (1990), Fromm, et al., *Bio/Technology*, 8:833 (1990), Koziel et al., *Bio/Technology,* 11:194 (1993), and Armstrong, et al., *Crop Science,* 35:550-557 (1995)); oat (Somers, et al., *Bio/Technology,* 10:1589 (1992)); orchard grass (Horn, et al., *Plant Cell Rep.* 7:469 (1988)); rye (De la Pena, et al., *Nature*, 325:274 (1987)); sugarcane (Bower and Birch, *Plant Journal*, 2:409 (1992)); tall fescue (Wang, et al., *Bio/Technology,* 10:691 (1992)); and wheat (Vasil, et al., *Bio/Technology,* 10:667 (1992) and U.S. Pat. No. 5,631,152).

The regeneration, development, and cultivation of plants from transformed plant protoplast or explants is well known in the art (see, for example, Weissbach and Weissbach, *Methods for Plant Molecular Biology*, (Eds.), Academic Press, Inc., San Diego, Calif. (1988) and Horsch et al., *Science,* 227:1229-1231 (1985)). Transformed cells are generally cultured in the presence of a selective media, which selects for the successfully transformed cells and induces the regeneration of plant shoots and roots into intact plants (Fraley, et al., *Proc. Natl. Acad. Sci. U.S.A.*, 80: 4803 (1983)). Transformed plants are typically obtained within two to four months.

The regenerated transgenic plants are self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, Calif., 50-98 (1960); Simmonds, *Principles of crop improvement*, Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses,* 2nd Edition, Monograph., 16:249 (1987); Fehr, *Principles of variety development, Theory and Technique*, (Vol 1) and *Crop Species Soybean* (Vol 2), Iowa State Univ., Macmillan Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used transgene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Regulatory elements useful to drive expression of an operably linked transcribable polynucleotide in transgenic plants were isolated, and the expression pattern of these regulatory elements operably linked to a transcribable polynucleotide molecule was analyzed in transgenic corn plants.

Example 1

Identification and Cloning of Regulatory Elements

Novel regulatory elements were identified and isolated from genomic DNA of the monocot species, Foxtail millet (Setaria italica (L.) Beauv). EST sequence was used to design primers, which were then used with GenomeWalker™ (Clontech Laboratories, Inc, Mountain View, Calif.) libraries constructed following the manufacturer's protocol to clone the 5' region of the corresponding genomic DNA sequence. This cloned region contained the 5' UTR sequence upstream of the protein-coding region for each gene from S. italica. Using this sequence, regulatory elements were bioinformatically identified within the 5' UTR for each gene. Bioinformatic analysis was used to identify the transcriptional start site (TSS) and any bi-directionality, introns, or upstream coding sequence present in the sequence. Using the results of this analysis, regulatory elements were defined within the 5' UTR sequence. Primers were then designed to amplify the regulatory elements. The corresponding DNA molecule for each regulatory element was amplified using standard polymerase chain reaction conditions with primers containing unique restriction enzyme sites and genomic DNA isolated from S. italica. The resulting DNA fragments were ligated into a base plant expression vector using standard restriction enzyme digestion of compatible restriction sites and DNA ligation methods. The resulting plant expression vectors contained a right border region from Agrobacterium tumefaciens (B-AGRtu.right border), test regulatory element(s) operably linked to an intron derived from the HSP70 heat shock protein of Zea mays, operably linked to a coding sequence for β-glucuronidase (GUS), operably linked to the Nopaline synthase 3' termination region from A. tumefaciens, and a left border region from A. tumefaciens (B-AGRtu.left border).

Sequences of the regulatory elements are provided herein as SEQ ID NO: 1-20 and are listed in Table 1 below. Promoter sequences are provided herein as SEQ ID NO: 2, 5, 8, 10, 13, and 20. Leader sequences are provided herein as SEQ ID NO: 3, 6, 11, and 16. Sequences provided herein as SEQ ID NO: 1, 4, 7, 9, 12, 14, 17, and 19 are an operably linked promoter and leader sequence.

TABLE 1

Regulatory Elements.

| SEQ ID | Annotation | cDNA Annotation |
|---|---|---|
| 1 | EXP-SETit.TIP | Tonoplast Intrinsic Protein |
| 2 | P-SETit.Tip-1:1:1 | Tonoplast Intrinsic Protein |
| 3 | L-SETit.Tip-1:1:1 | Tonoplast Intrinsic Protein |
| 4 | EXP-SETit.Mtha | Metallothionein-like protein |
| 5 | P-SETit.Mtha-1:1:1 | Metallothionein-like protein |
| 6 | L-SETit.Mth-1:1:1 | Metallothionein-like protein |
| 7 | EXP-SETit.Mthb | Metallothionein-like protein |

TABLE 1-continued

Regulatory Elements.

| SEQ ID | Annotation | cDNA Annotation |
|---|---|---|
| 8 | P-SETit.Mthb-1:1:2 | Metallothionein-like protein |
| 9 | EXP-SETit.DRPa | Dehydration Related Protein a |
| 10 | P-SETit.DRPa-1:1:1 | Dehydration Related Protein a |
| 11 | L-SETit.DRP-1:1:2 | Dehydration Related Protein a/b |
| 12 | EXP-SETit.DRPb | Dehydration Related Protein b |
| 13 | P-SETit.DRPb-1:1:1 | Dehydration Related Protein b |
| 14 | EXP-SETit.Rcc3-1 | Lipid Transfer Protein |
| 15 | P-SETit.Rcc3-1:1:1 | Lipid Transfer Protein |
| 16 | L-SETit.Rcc3-1:1:2 | Lipid Transfer Protein |
| 17 | EXP-SETit.Rcc3-10 | Lipid Transfer Protein |
| 18 | P-SETit.Rcc3-1:1:10 | Lipid Transfer Protein |
| 19 | EXP-SETit.Rcc3-11 | Lipid Transfer Protein |
| 20 | P-SETit.Rcc3-1:1:11 | Lipid Transfer Protein |

The expression element, EXP-SETit.TIP (SEQ ID NO: 1) is comprised of the P-SETit.Tip-1:1:1 promoter (SEQ ID NO: 2) and the L-SETit.Tip-1:1:1 leader (SEQ ID NO: 3).

For the regulatory elements from the Lipid Transfer Protein gene, three promoter variants were designed (FIG. 1). P-SETit.Rcc3-1:1:1 a 2062 nucleotide version (SEQ ID NO:15); P-SETit.Rcc3-1:1:10 a 1563 nucleotide version (SEQ ID NO:18); and P-SETit.Rcc3-1:1:11 a 915 nucleotide version (SEQ ID NO:20). The expression element, EXP-SETit.Rcc3-1 (SEQ ID NO: 14) is comprised of the P-SETit.Rcc3-1:1:1 promoter (SEQ ID NO: 15) and the P-SETit.Rcc3-1:1:2 leader (SEQ ID NO: 16). The expression element, EXP-SETit.Rcc3-10 (SEQ ID NO: 17) is comprised of the P-SETit.Rcc3-1:1:10 promoter (SEQ ID NO: 18) and the L-SETit.Rcc3-1:1:2 leader (SEQ ID NO: 16). The expression element, EXP-SETit.Rcc3-11 (SEQ ID NO: 19) is comprised of the P-SETit.Rcc3-1:1:11 promoter (SEQ ID NO: 20) and the P-SETit.Rcc3-1:1:2 leader (SEQ ID NO: 16).

Figure 2:
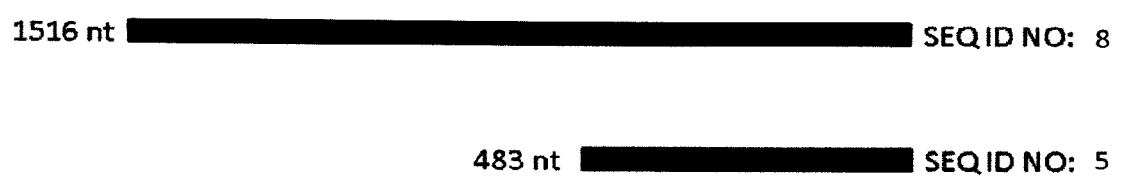

For the regulatory elements from the Metallothionein-like protein gene, two promoter variants were designed (FIG. 2). P-SETit.Mtha-1:1:1 is a shorter 483 nucleotide version; P-SETit.Mthb-1:1:2 is a longer 1516 nucleotide version of this. The expression element, EXP-SETit.Mtha (SEQ ID NO: 4) is comprised of the P-SETit.Mtha-1:1:1 promoter (SEQ ID NO: 5) and the L-SETit.Mth-1:1:1 leader (SEQ ID NO: 6). The expression element, EXP-SETit.Mthb (SEQ ID NO: 7) is comprised of the P-SETit.Mthb-1:1:2 promoter (SEQ ID NO: 8) and the L-SETit.Mth-1:1:1 leader (SEQ ID NO: 5).

For the regulatory elements from the Dehydration Related Protein gene, the regulatory elements from two allelic variants were isolated (FIGS. 3A and 3B). The two allelic variants have identical leader sequences, but the promoter sequences are variants with several base changes and insertion/deletions when aligned. The expression element, EXP-SETit.DRPa (SEQ ID NO: 9) is comprised of the P-SETit.DRP-1:1:1 promoter (SEQ ID NO: 10) and the L-SETit.DRP-1:1:2 leader (SEQ ID NO: 11). The expression element, EXP-SETit.DRPb (SEQ ID NO: 12) is comprised of the P-SETit.DRPb-1:1:1 promoter (SEQ ID NO: 13) and the L-SETit.DRP-1:1:2 leader (SEQ ID NO: 11).

Example 2

Analysis of Regulatory Elements Driving GUS in Transgenic Corn

Corn plants were transformed with plant expression vectors containing the test regulatory elements driving expression of the β-glucuronidase (GUS) transgene, and the resulting plants were analyzed for GUS protein expression.

Corn plants were transformed with plant GUS expression constructs, pMON101552 (EXP-SETit.TIP, SEQ ID NO: 1), pMON99662 (EXP-SETit.Mtha, SEQ ID NO: 4), and pMON99663 (EXP-SETit.DRPa, SEQ ID NO: 9). Plants were transformed using particle bombardment methods known to those skilled in the art and corn H99 immature zygotic embryos to produce transgenic maize plants. Briefly, ears of maize H99 plants were collected 10-13 days after pollination from greenhouse-grown plants and sterilized. Immature zygotic embryos of 1.2-1.5 mm were excised from the ear and incubated at 28° Celsius in the dark for 3-5 days before use as target tissue for bombardment. The plant transformation vector containing the selectable marker for kanamycin resistance (NPTII gene) and the GUS expression cassette was digested with restriction endonucleases. A single DNA fragment containing both the selectable marker and GUS expression cassette was gel purified and used to coat 0.6 micron gold particles (Catalog #165-2262 Bio-Rad, Hercules, Calif.) for bombardment. Macro-carriers were loaded with the DNA-coated gold particles (Catalog #165-2335 Bio-Rad, Hercules Calif.). The embryos were transferred onto osmotic medium, scutellum side up. A PDS 1000/He biolistic gun was used for transformation (Catalog #165-2257 Bio-Rad, Hercules Calif.). Bombarded immature embryos were cultured and transgenic calli were selected and transferred to tissue regeneration medium. Transgenic corn plants were regenerated from the transgenic calli and transferred to the greenhouse.

Histochemical GUS analysis was used for qualitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues. The $R_0$ plants were inspected for expression in the roots and leaves. The regulatory elements EXP-SETit.TIP (SEQ ID NO: 1), EXP-SETit.Mtha (SEQ ID NO: 4), and EXP-SETit.DRPa (SEQ ID NO: 9) demonstrated GUS expression in both roots and leaves in the $R_0$ transformants.

Plants transformed with GUS expression driven by either EXP-SETit.TIP (SEQ ID NO: 1) or EXP-SETit.Mtha (SEQ ID NO: 4) were crossed with non-transformed H99 plants to produce an $F_1$ population of transformants. GUS expression levels were measured in selected tissues over the course of development. The $F_1$ tissues used for this study included: imbibed seed embryo, imbibed seed endosperm, root (3 days after germination), coleoptiles (3 days after germination), V3 main and crown root, V3 leaf, V7 seminal and crown root, V7 mature leaf, VT (at tasseling, prior to reproduction) seminal root, VT internode, VT cob, VT anther, VT pollen, VT silk, kernel 7 days after pollination, embryo on 21 days after pollination, endosperm 21 days after pollination, embryo 35 days after pollination, endosperm 35 days after pollination. $F_1$ GUS expression was seen in all tissues studied for both for events transformed EXP-SETit.TIP (SEQ ID NO: 1) and EXP-SETit.Mtha (SEQ ID NO: 4).

Example 3

Analysis of Regulatory Elements Driving TIC809 in Transgenic Corn

Corn plants were transformed with plant expression vectors containing the test regulatory elements driving expression of the TIC809 transgene, and the resulting plants were analyzed for TIC809 protein expression.

The regulatory elements were operably linked to the insect toxin transgene, TIC809 (PCTUS2006/033867) in plant transformation vectors. The transgene cassette was comprised of regulatory element(s) operably linked to an intron derived from the HSP70 heat shock protein of *Zea mays*, operably linked to the TIC809 transgene, operably linked to a 3' UTR derived from the *Triticum aestivum* L. HSP17 gene. The plant transformation vectors also contained a glyphosate tolerance selectable marker for selection of transformed plant cells.

Corn tissue from variety LH244 was transformed using *A. tumefaciens* mediated transformation with plasmids, pMON70539 (EXP-SETit.TIP, SEQ ID NO: 1), pMON70540 (EXP-SETit.Mtha, SEQ ID NO: 4), and pMON70538 (EXP-SETit.DRPa, SEQ ID NO: 9) using methods known in the art. $R_0$ plants were regenerated from the transformed corn tissue and tested to confirm the presence and intactness of the TIC809 transgene. Leaves and roots from these plants were analyzed at the V4 or V6 stage using a TIC809 Enzyme-Linked ImmunoSorbent Assay (ELISA) to determine the levels of TIC809 protein accumulation. Protein values were determined using a TIC809 reference sample and expressed in units of parts per million (ppm). ELISA data is presented in Table 2 below where "N" indicates the number of plants tested.

TABLE 2

TIC809 $R_0$ ELISA Data.

| Element Name | SEQ ID NO | Vector | Root (ppm) | Leaf (ppm) | N |
|---|---|---|---|---|---|
| EXP-SETit.TIP | 1 | pMON70539 | 3 | 6 | 26 |
| EXP-SETit.Mtha | 4 | pMON70540 | 3 | 8 | 20 |
| EXP-SETit.DRPa | 9 | pMON70538 | 1 | 2 | 24 |

TIC809 expression, driven by the expression elements, EXP-SETit.TIP (SEQ ID NO: 1), EXP-SETit.Mtha (SEQ ID NO: 4), and EXP-SETit.DRPa (SEQ ID NO: 9) was seen in both roots and leaves, thus demonstrating the ability of the regulatory elements EXP-SETit.TIP, EXP-SETit.Mtha, and EXP-SETit.DRPa to modulate transcription of an operably linked transgene of agronomic interest in plants. The average TIC809 expression driven by EXP-SETit.TIP (SEQ ID NO: 1), EXP-SETit.Mtha (SEQ ID NO: 4), and EXP-SETit.DRPa (SEQ ID NO: 9) was at least 2 fold or higher in the leaf relative to root for all three constructs.

Transformed R0 plants containing the vectors pMON70539 (EXP-SETit.TIP, SEQ ID NO: 1), pMON70540 (EXP-SETit.Mtha, SEQ ID NO: 4), and pMON70538 (EXP-SETit.DRPa, SEQ ID NO: 9) were crossed with variety LH59, using LH59 as the female plant and transformed LH244 as the male, to produce transformed $F_1$ populations. For plants containing EXP-SETit.TIP (SEQ ID NO: 1) and EXP-SETit.Mtha (SEQ ID NO: 4), TIC809 protein levels were then measured using ELISA in $F_1$ leaves at V3, V7, and VT stages; in roots at V3 and V7 stages; in reproductive tissues around VT stage (anther, pollen and silk); and in the developing seed or kernel. The ELISA results are expressed in parts per million (ppm) with standard error measurements indicated as "SE" and presented in Table 3 below. For plants containing EXP-SETit.DRPa (SEQ ID NO: 9), TIC809 protein levels were measured in roots using ELISA with tissue taken at V9 stage. The ELISA results are expressed in parts per million (ppm) and presented in Table 4 below.

TABLE 3

TIC809 $F_1$ ELISA Data for EXP-SETit.TIP and EXP-SETit.Mtha.

|  | EXP-SETit.TIP | | EXP-SETiT.Mtha | |
| --- | --- | --- | --- | --- |
| Tissue | ppm | SE | ppm | SE |
| Leaf V3 | 1.138 | 0.32 | 1.312 | 0.46 |
| Root V3 | 1.254 | 0.41 | 1.242 | 0.39 |
| Stalk V3 | 0.694 | 0.14 | 0.407 | 0.19 |
| Leaf V7 | 0.879 | 0.31 | 1.295 | 0.31 |
| Root V7 | 0.755 | 0.35 | 1.185 | 0.46 |
| Leaf VT | 0.308 | 0.17 | 0.457 | 0.35 |
| Anther | 0.323 | 0.06 | 0.364 | 0.1 |
| Silk | 0.249 | 0.1 | 0.222 | 0.05 |
| Pollen | 0.315 | 0.16 | 0.231 | 0.01 |
| Seed | 0.138 | 0.02 | 0 | 0 |

Average TIC809 protein expression levels driven by the regulatory elements, EXP-SETit.TIP (SEQ ID NO: 1) and EXP-SETit.Mtha (SEQ ID NO: 4) in the F1 populations were consistent with the expression levels observed in the R0 transformants, confirming the ability of the TIP and Mtha regulatory elements to drive expression of an operably linked transgene. EXP-SETit.TIP (SEQ ID NO: 1) appears to have its highest level of expression at V3 in the roots and leaves, with expression declining by V7 stage and low in the reproductive tissues and developing seed. EXP-SETit.Mtha (SEQ ID NO: 4) shows consistent expression of TIC809 in the roots and leaves between V3 and V7 stage, with a decline in expression in the VT stage leaf, lower expression in the reproductive tissue, and no expression in the developing seed.

TABLE 4

TIC809 F1 ELISA Data for EXP-SETit.DRPa.

| $F_1$ Cross Tissue | ppm |
| --- | --- |
| LH59/ZM_S198227 | 0.95 |
| LH59/ZM_S198230 | 2.69 |
| LH59/ZM_S198235 | 0.5 |
| LH59/ZM_S199429 | 1.26 |
| LH59/ZM_S201032 | 1.09 |
| LH59/ZM_S201049 | 0.64 |
| Average TIC809 Expression | 1.19 |
| Standard Error | 0.79 |

Average TIC809 protein expression levels driven by the regulatory element, EXP-SETit.DRPa (SEQ ID NO: 9) in the F1 population roots were consistent with the expression levels observed in the $R_0$ transformants, confirming the ability of the DRPa regulatory elements to provide root expression of an operably linked transgene.

$R_0$ populations of plants transformed with pMON120408 (EXP-SETit.Rcc3-1, SEQ ID NO: 14), pMON120407 (EXP-SETit.Rcc3-10, SEQ ID NO: 17), and pMON120410 (EXP-SETit.Rcc3-11, SEQ ID NO: 19) were produced as described above. TIC809 protein levels in these plants were measured in leaves and roots using ELISA with tissue taken at the V4 or V6 stage. The ELISA results are expressed in parts per million (ppm) and are presented in Table 5 below.

TABLE 5

TIC809 $R_0$ ELISA Data for EXP-SETit.Rcc3-1, EXP-SETit.Rcc3-10, and EXP-SETit.Rcc3-11.

| Element Name | Event | Root (ppm) | Leaf (ppm) |
| --- | --- | --- | --- |
| EXP-SETit.Rcc3-1 (SEQ ID NO: 14) | 1 | 0.292 | 0 |
| EXP-SETit.Rcc3-1 (SEQ ID NO: 14) | 2 | 2.79 | 0 |
| EXP-SETit.Rcc3-1 (SEQ ID NO: 14) | 3 | 1.171 | 0 |
| EXP-SETit.Rcc3-1 (SEQ ID NO: 14) | Average | 1.42 | 0 |
| EXP-SETit.Rcc3-10 (SEQ ID NO: 17) | 1 | 2.129 | 0 |
| EXP-SETit.Rcc3-10 (SEQ ID NO: 17) | 2 | 1.793 | 0 |
| EXP-SETit.Rcc3-10 (SEQ ID NO: 17) | 3 | 0.425 | 0 |
| EXP-SETit.Rcc3-10 (SEQ ID NO: 17) | 4 | 0.677 | 0 |
| EXP-SETit.Rcc3-10 (SEQ ID NO: 17) | 5 | 0.877 | 0 |
| EXP-SETit.Rcc3-10 (SEQ ID NO: 17) | 6 | 1.847 | 0 |
| EXP-SETit.Rcc3-10 (SEQ ID NO: 17) | 7 | 1.479 | 0 |
| EXP-SETit.Rcc3-10 (SEQ ID NO: 17) | 8 | 0.359 | 0 |
| EXP-SETit.Rcc3-10 (SEQ ID NO: 17) | 9 | 1.84 | 0 |
| EXP-SETit.Rcc3-10 (SEQ ID NO: 17) | 10 | 3.309 | 0 |
| EXP-SETit.Rcc3-10 (SEQ ID NO: 17) | 11 | 1.589 | 0 |
| EXP-SETit.Rcc3-10 (SEQ ID NO: 17) | 12 | 3.652 | 0.294 |
| EXP-SETit.Rcc3-10 (SEQ ID NO: 17) | 13 | 1.019 | 0 |
| EXP-SETit.Rcc3-10 (SEQ ID NO: 17) | 14 | 2.715 | 0.56 |
| EXP-SETit.Rcc3-10 (SEQ ID NO: 17) | 15 | 0.981 | 0 |
| EXP-SETit.Rcc3-10 (SEQ ID NO: 17) | 16 | 3.147 | 0.317 |
| EXP-SETit.Rcc3-10 (SEQ ID NO: 17) | Average | 1.74 | 0.07 |
| EXP-SETit.Rcc3-11 (SEQ ID NO: 19) | 1 | 2.356 | 0 |
| EXP-SETit.Rcc3-11 (SEQ ID NO: 19) | 2 | 2.343 | 0 |
| EXP-SETit.Rcc3-11 (SEQ ID NO: 19) | 3 | 1.465 | 0 |
| EXP-SETit.Rcc3-11 (SEQ ID NO: 19) | 4 | 2.271 | 0 |
| EXP-SETit.Rcc3-11 (SEQ ID NO: 19) | 5 | 0.247 | 0 |
| EXP-SETit.Rcc3-11 (SEQ ID NO: 19) | 6 | 2.949 | 0 |
| EXP-SETit.Rcc3-11 (SEQ ID NO: 19) | 7 | 3.36 | 0 |
| EXP-SETit.Rcc3-11 (SEQ ID NO: 19) | 8 | 4.771 | 0 |
| EXP-SETit.Rcc3-11 (SEQ ID NO: 19) | 9 | 1.757 | 0 |
| EXP-SETit.Rcc3-11 (SEQ ID NO: 19) | 10 | 2.255 | 0 |
| EXP-SETit.Rcc3-11 (SEQ ID NO: 19) | 11 | 3.314 | 0 |
| EXP-SETit.Rcc3-11 (SEQ ID NO: 19) | 12 | 4.958 | 0 |
| EXP-SETit.Rcc3-11 (SEQ ID NO: 19) | 13 | 0.232 | 0 |
| EXP-SETit.Rcc3-11 (SEQ ID NO: 19) | 14 | 1.503 | 0 |
| EXP-SETit.Rcc3-11 (SEQ ID NO: 19) | 15 | 1.425 | 0 |
| EXP-SETit.Rcc3-11 (SEQ ID NO: 19) | 16 | 3.6 | 0 |
| EXP-SETit.Rcc3-11 (SEQ ID NO: 19) | 17 | 3.533 | 0 |
| EXP-SETit.Rcc3-11 (SEQ ID NO: 19) | 18 | 2.158 | 0 |
| EXP-SETit.Rcc3-11 (SEQ ID NO: 19) | Average | 2.47 | 0 |

Expression of TIC809 when driven by the expression elements variants EXP-SETit.Rcc3-1 (SEQ ID NO: 14), EXP-SETit.Rcc3-10 (SEQ ID NO: 17), and EXP-SETit.Rcc3-11 (SEQ ID NO: 19) was strong in roots and weak or absent in leaves. Low or no leaf expression was observed for the three SETit.Rcc3 variants with the exception of three transformed events in which the expression element variant, EXP-SETit.Rcc3-10 (SEQ ID NO: 17) showed a low level of TIC809 expression in leaves. The average root expression of the TIC809 protein was higher using the expression element variant, EXP-SETit.Rcc3-11 (SEQ ID NO: 19) than the EXP-SETit.Rcc3-1 (SEQ ID NO: 14) and EXP-SETit.Rcc3-10 (SEQ ID NO: 17) variants, but all three variants provided root expression of the operably linked transgene.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

We claim:

1. A DNA molecule comprising a regulatory element having a DNA sequence selected from the group consisting of: SEQ ID NOs: 1 and 2,
wherein said regulatory element is operably linked to a heterologous transcribable polynucleotide molecule.

2. The DNA molecule of claim 1, wherein the transcribable polynucleotide molecule is a gene of agronomic interest.

3. The DNA molecule of claim 1, wherein the transcribable polynucleotide molecule is a gene capable of providing herbicide resistance in plants.

4. The DNA molecule of claim 1, wherein the transcribable polynucleotide molecule is a gene capable of providing plant pest control in plants.

5. A transgenic plant cell stably transformed with the DNA molecule of claim 1.

6. The transgenic plant cell of claim 5, wherein said transgenic plant cell is a monocotyledonous plant cell.

7. A transgenic plant stably transformed with the DNA molecule of claim 1.

8. A plant part of the transgenic plant of claim 7, wherein the plant part comprises the DNA molecule.

9. A seed of the transgenic plant of claim 7, wherein the seed comprises the DNA molecule.

\* \* \* \* \*

SEQUENCE LISTING

<160> NUMBER OF SEQ ID NOS: 20

<210> SEQ ID NO 1
<211> LENGTH: 981
<212> TYPE: DNA
<213> ORGANISM: Setaria italica

<400> SEQUENCE: 1

| | |
|---|---|
| tgtactgtca tattgtcgtg gtttttcaat tgctgtacct gatgcaaacg taatgggttt | 60 |
| actaatcttg cacccgccgg cttcaaaatg aagagtgcta atttggtcca cgtcaccatc | 120 |
| accggttcga actgtctaga atggcaggca aagatgattg acaggcatg cagggaaaaa | 180 |
| gagcaccgtt gacgatgtat gcgagttccc accattgcga gcaatgatta tcagccacac | 240 |
| gacttactct tcagagctaa ccactgccat gcagagaaaa agtgaatcat attgtcatga | 300 |
| tctacaacga agtgaaacaa tcaggcatgc taaagtgctg aaactttact gatctctcat | 360 |
| gttggacaac aaagaatacg ggaatacatc agcaacgcaa ctcttgagct ttgcttgccg | 420 |
| aatgaccagc tagaatttcc aagcatttac agaaacatga ctttaagttt cagaaaaaca | 480 |
| aatacaaggc cactaaataa gcgtggggat aacatatcct ccagatgaca ggcaatctgc | 540 |
| aacttgcagc cattcaaatg tacgattaac aaaatattta agcgccacat gagataatat | 600 |
| atcctccaat tagggccttt agtattgtca ttagctcata accatggtgc atcctcacat | 660 |
| ggacgctgca taagaagttc ataatagcaa cagacatatg aacaaagcat ggtgcgcctg | 720 |
| cccggccgga ctagctagta ctaccaatca tggaataagc tagtacccta aatgaaatta | 780 |
| aaatggtttt tagcgattat ccacgccgtc cagaatactc taatccacaa gttgaggccg | 840 |
| cccatgaagc cgcgagaggg cgacgccatg tgtataaaag gggcctaagc tgagtggact | 900 |
| tgctgcatca gattagtaag caatctcaag cgcagagagc caaagctttc ggtgtagctc | 960 |
| gaagagcaaa gcgaaggcaa g | 981 |

<210> SEQ ID NO 2
<211> LENGTH: 917
<212> TYPE: DNA
<213> ORGANISM: Setaria italica

<400> SEQUENCE: 2

| | |
|---|---|
| tgtactgtca tattgtcgtg gtttttcaat tgctgtacct gatgcaaacg taatgggttt | 60 |
| actaatcttg cacccgccgg cttcaaaatg aagagtgcta atttggtcca cgtcaccatc | 120 |
| accggttcga actgtctaga atggcaggca aagatgattg acaggcatg cagggaaaaa | 180 |
| gagcaccgtt gacgatgtat gcgagttccc accattgcga gcaatgatta tcagccacac | 240 |
| gacttactct tcagagctaa ccactgccat gcagagaaaa agtgaatcat attgtcatga | 300 |
| tctacaacga agtgaaacaa tcaggcatgc taaagtgctg aaactttact gatctctcat | 360 |
| gttggacaac aaagaatacg ggaatacatc agcaacgcaa ctcttgagct ttgcttgccg | 420 |
| aatgaccagc tagaatttcc aagcatttac agaaacatga ctttaagttt cagaaaaaca | 480 |
| aatacaaggc cactaaataa gcgtggggat aacatatcct ccagatgaca ggcaatctgc | 540 |
| aacttgcagc cattcaaatg tacgattaac aaaatattta agcgccacat gagataatat | 600 |
| atcctccaat tagggccttt agtattgtca ttagctcata accatggtgc atcctcacat | 660 |
| ggacgctgca taagaagttc ataatagcaa cagacatatg aacaaagcat ggtgcgcctg | 720 |
| cccggccgga ctagctagta ctaccaatca tggaataagc tagtacccta aatgaaatta | 780 |
| aaatggtttt tagcgattat ccacgccgtc cagaatactc taatccacaa gttgaggccg | 840 |

```
cccatgaagc cgcgagaggg cgacgccatg tgtataaaag gggcctaagc tgagtggact    900
tgctgcatca gattagt                                                   917
```

<210> SEQ ID NO 3
<211> LENGTH: 64
<212> TYPE: DNA
<213> ORGANISM: Setaria italica

<400> SEQUENCE: 3

```
aagcaatctc aagcgcagag agccaaagct ttcggtgtag ctcgaagagc aaagcgaagg     60
caag                                                                  64
```

<210> SEQ ID NO 4
<211> LENGTH: 550
<212> TYPE: DNA
<213> ORGANISM: Setaria italica

<400> SEQUENCE: 4

```
taaggaaata taaaagaag aaactacttg tttttgcaat gataacgtac atacagatat      60
ttctaaagcc atcaagtacc tagcttgtct aaataacaag tgtgtcctgg aacaagtatc    120
gagtacctga aagcaacctg ctttgaattg gaaaggataa aaattcgaca aggaacgaac    180
aaaggaggca catttcttgc cggccagaaa ctattgggtc tttgcatcct tgtgaattga    240
taaacgtgct ggtgtgtttc aatgatgtcc atgagatggg aatacaaagt caagcacgcc    300
ttattacctt attgtgtggc tctgtctgca gaaagcaacc gggcgcattt tcttccgata    360
ccgtggttac tttcaaattg gaagacagag acgtacacac aaggcaataa ttcagggaac    420
aattccatcc atccactgct ataaaaggcg gtgttggggt gtgggtctc ttcagttcag     480 tgtgctcaag caatctcaaa gaacttgtct tctccatcca caccgagttt tcggcttct    540 tgacttgaag                                                           550
```

<210> SEQ ID NO 5
<211> LENGTH: 483
<212> TYPE: DNA
<213> ORGANISM: Setaria italica

<400> SEQUENCE: 5

```
taaggaaata taaaagaag aaactacttg tttttgcaat gataacgtac atacagatat      60
ttctaaagcc atcaagtacc tagcttgtct aaataacaag tgtgtcctgg aacaagtatc    120
gagtacctga aagcaacctg ctttgaattg gaaaggataa aaattcgaca aggaacgaac    180
aaaggaggca catttcttgc cggccagaaa ctattgggtc tttgcatcct tgtgaattga    240
taaacgtgct ggtgtgtttc aatgatgtcc atgagatggg aatacaaagt caagcacgcc    300
ttattacctt attgtgtggc tctgtctgca gaaagcaacc gggcgcattt tcttccgata    360
ccgtggttac tttcaaattg gaagacagag acgtacacac aaggcaataa ttcagggaac    420
aattccatcc atccactgct ataaaaggcg gtgttggggt gtgggtctc ttcagttcag     480 tgt                                                                  483
```

<210> SEQ ID NO 6
<211> LENGTH: 67
<212> TYPE: DNA
<213> ORGANISM: Setaria italica

<400> SEQUENCE: 6
gctcaagcaa tctcaaagaa cttgtcttct ccatccacac cgagttttc ggcttcttga    60 cttgaag                                                             67

<210> SEQ ID NO 7
<211> LENGTH: 1583
<212> TYPE: DNA
<213> ORGANISM: Setaria italica

<400> SEQUENCE: 7
cctcttcctt tattttttgcc atcagcgtcg ttgttgaact ctcgtgcctg ttaaagatgt    60
gtgtgttccg ctctttccaa atttcccata taatgagtag agtgagactt tgcatagcct   120
tgcgcggtaa gtccagtatt gtagttatag aagtccatca ttccaatgca ttggatgagg   180
gttgccatgc agttggtctg atgcttggct gcgctaacca tgttgccgtt aaatcccata   240
tcctccttgt gttcctgcac ttagcctaga tgtggtgact agtttccatg gtttgtctgc   300
atagggtgca agtggcgttg tatggccatc cacgtttagc ctgcctatcc acggaccaaa   360
ctcagttttg tgtaattagc cgcaagaaga atttgcattt tgccggcgcc cacgttttcc   420
agacagaaga gatttctggt gtttcgatgc agcccaggaa ctgtgcttta tatgccgatg   480
ctattgtata catgacggat cttgttagtt tctagaagat agtatcctct tccacttatc   540
gaagctcctg accatagccc atagggcgaa cgatgctaga tgctaaatgt gaagtggtga   600
tgctgttgtc gatattgagg tcacagatcc agttgttact gatagcatcg tgaactgtcc   660
tattttgtct tcttgaaatg tcgaagagga gtggagcaat gtccttaggt gctggccatg   720
tagctagcca gaagtccaga agctagcctt tttgccatca ccaagagtga taaccatgca   780
ggcaacaaat acttgcatgt ctgtctcgtc gcatgggatt tctatgttgg tccagggttt   840
ttccggtgat gcctactcat gccaaagcca cctcagacgg agggctcgtg cgaatttctc   900
gaggtcagcc cctcgtattg cttcagtagg caggttttcg tccagttgac tttacattta   960
ccctcggtta gctgttggtc tcccgctcag aggaattttt tacggatctt gtctaagtct  1020
tggagcccct cttaaggaa ataataaaag aagaaactac ttgttttttgc aatgataacg  1080 tacatacaga tatttctaaa gccatcaagt acctagcttg tctaaataac aagtgtgtcc  1140
tggaacaagt atcgagtacc tgaaagcaac ctgctttgaa ttggaaagga taaaaattcg  1200
acaaggaacg aacaaaggag gcacatttct tgccggccag aaactattgg gtctttgcat  1260
ccttgtgaat tgataaacgt gctggtgtgt ttcaatgatg tccatgagat gggaatacaa  1320
agtcaagcac gccttattac cttattgtgt ggctctgtct gcagaaagca accgggcgca  1380
ttttcttccg ataccgtggt tactttcaaa ttggaagaca gagacgtaca cacaaggcaa  1440
taattcaggg aacaattcca tccatccact gctataaaag gcggtgttgg ggtgttgggt  1500
ctcttcagtt cagtgtgctc aagcaatctc aaagaacttg tcttctccat ccacaccgag  1560
tttttcggct tcttgacttg aag                                          1583

<210> SEQ ID NO 8
<211> LENGTH: 1516
<212> TYPE: DNA
<213> ORGANISM: Setaria italica

<400> SEQUENCE: 8
cctcttcctt tattttttgcc atcagcgtcg ttgttgaact ctcgtgcctg ttaaagatgt    60
gtgtgttccg ctctttccaa atttcccata taatgagtag agtgagactt tgcatagcct   120
tgcgcggtaa gtccagtatt gtagttatag aagtccatca ttccaatgca ttggatgagg   180

-continued

```
gttgccatgc agttggtctg atgcttggct gcgctaacca tgttgccgtt aaatcccata        240
tcctccttgt gttcctgcac ttagcctaga tgtggtgact agtttccatg gtttgtctgc        300
atagggtgca agtggcgttg tatggccatc cacgtttagc ctgcctatcc acggaccaaa        360
ctcagttttg tgtaattagc cgcaagaaga atttgcattt tgccggcgcc acgttttcc         420 agacagaaga gatttctggt gtttcgatgc agcccaggaa ctgtgcttta tatgccgatg        480
ctattgtata catgacggat cttgttagtt tctagaagat agtatcctct tccacttatc        540
gaagctcctg accatagccc atagggcgaa cgatgctaga tgctaaatgt gaagtggtga        600
tgctgttgtc gatattgagg tcacagatcc agttgttact gatagcatcg tgaactgtcc        660
tattttgtct tcttgaaatg tcgaagagga gtggagcaat gtccttaggt gctggccatg        720
tagctagcca gaagtccaga agctagcctt tttgccatca ccaagagtga taaccatgca        780
ggcaacaaat acttgcatgt ctgtctcgtc gcatgggatt tctatgttgg tccagggttt        840
ttccggtgat gcctactcat gccaaagcca cctcagacgg agggctcgtg cgaatttctc        900
gaggtcagcc cctcgtattg cttcagtagg caggttttcg tccagttgac tttacattta        960
ccctcggtta gctgttggtc tcccgctcag aggaattttt tacgatcttt gtctaagtct        1020
tggagcccct ctttaaggaa ataataaaag aagaaactac ttgttttttgc aatgataacg       1080 tacatacaga tatttctaaa gccatcaagt acctagcttg tctaaataac aagtgtgtcc        1140
tggaacaagt atcgagtacc tgaaagcaac ctgctttgaa ttggaaagga taaaaattcg        1200
acaaggaacg aacaaaggag gcacatttct tgccggccag aaactattgg gtctttgcat        1260
ccttgtgaat tgataaacgt gctggtgtgt ttcaatgatg tccatgagat gggaatacaa        1320
agtcaagcac gccttattac cttattgtgt ggctctgtct gcagaaagca accgggcgca        1380
ttttcttccg ataccgtggt tactttcaaa ttggaagaca gagacgtaca cacaaggcaa        1440
taattcaggg aacaattcca tccatccact gctataaaag gcggtgttgg ggtgttgggt        1500
ctcttcagtt cagtgt                                                        1516
```

<210> SEQ ID NO 9
<211> LENGTH: 1766
<212> TYPE: DNA
<213> ORGANISM: Setaria italica

<400> SEQUENCE: 9

```
tggtaaaatc aattcatatg cttatacttc aaaaaccaat ttatgtgtat atacttggaa         60
aaattagatt aagtatttca atttatttgc ttatatttca aaaataaatt cttgtgcata        120
tacttagaaa aattagatta agtatttcaa tttatttgct tatacttcaa aaatcaattc        180
ttgtgtatat acttacaaaa attagattaa gtatttcaat ttaattgctt atatttgaag        240
taagtcaatt gtgcaaaccc attgatctac tatatatgta ataaactttg ccaatgacac        300
agatgatgta caggaaagat agaatcttca agtggatttc ttctagacga ggtcataaat        360
ccagcggggg agtttcataa tgatgcatca aatctacagc accgtcagga ctcgggttta        420
gaatagtaga aatgatatgt gtacgcacaa tatgtctata tatatgtata atattattca        480
tatatgtgta tgcataatat gtatatatat aatagtatct taaatgtaat attgaagata        540
aatagaactt tatatatatt agcgtattag aagtagtata cgtatgaata tagaataaag        600
aaaaagaaaa taagaaaaga aaggaaaaaa acaaatcagt accggtcggg agaccaacc         660 ggcactaatt aggccccttta gtgccctccc gccacccttct cctccctctt ctctcgccgc      720
```

| | |
|---|---|
| cctctcctcc ctctcagctc ttcccgaccc cttcctctcc cactgccgcc ccctccctct | 780 |
| ctccgccgac caccatcgtc ctgcgtgatc tccctctcct caccctcggc tgcccctcct | 840 |
| ctccccttc gctcacccct cactcgtggc agtgaggagc agcggcaaca catagatccg | 900 |
| gtggtggcag tgcaggttcc agtgaagaag gagctagcac ggatccgacg aagaaggagc | 960 |
| tggttgcggt ggcgtaggtg gcggccctg gcggcgcggc ctcagcttcc tctccccgta | 1020 |
| cgcctctctc tctctctctc tatgagccgg atccggtagg accaaggcag ttggcggctg | 1080 |
| gtggggcggc aacggccaga tccagcgaga tgcggccggt cggatccggc gaggcagcgc | 1140 |
| aaggccgggg cgtaaggcgg ccggcagcac cattttttg ttttttaat aggccttcac | 1200 |
| cgccagttcc aaaaccagcg gtgatggggt atccccatca ctaccgaaag tcagacgatg | 1260 |
| gatccaaacc gacggtgaag actggtttgg agccggcagt gatgaacctc tggagtagtg | 1320 |
| cttatggctg ggggcattga cattcttttt actaactttc ttcctaccac gtagtatgca | 1380 |
| ataattgtac gtaatactag tagctgatga taagtttgat ataagactat caagcggtct | 1440 |
| cgacatttca caatctcgtg cagcacatgg acagctatac taacgagaag tcgaggacga | 1500 |
| cagcccaccg acttgacaaa tctgtacaaa atatgctaga aaatattgc accaatcaaa | 1560 |
| cattgcccat caaggccacc aaggatacat gatgacaacg ccaatcaga cttcaaagat | 1620 |
| atctcaacat catacacaca gaaggaagag atgatgactc cagtttaact ttcatcgacg | 1680 |
| actcctataa atacgaccct cttcctgtac gcctcctcat tccaacacag gaacgggatt | 1740 |
| cttccttctt ctggccatta gctcca | 1766 |

<210> SEQ ID NO 10
<211> LENGTH: 1726
<212> TYPE: DNA
<213> ORGANISM: Setaria italica

<400> SEQUENCE: 10

| | |
|---|---|
| tggtaaaatc aattcatatg cttatacttc aaaaaccaat ttatgtgtat atacttggaa | 60 |
| aaattagatt aagtatttca atttatttgc ttatatttca aaataaatt cttgtgcata | 120 |
| tacttagaaa aattagatta agtatttcaa tttatttgct tatacttcaa aaatcaattc | 180 |
| ttgtgtatat acttacaaaa attagattaa gtatttcaat ttaattgctt atatttgaag | 240 |
| taagtcaatt gtgcaaaccc attgatctac tatatatgta ataaactttg ccaatgacac | 300 |
| agatgatgta caggaaagat agaatcttca agtggatttc ttctagacga ggtcataaat | 360 |
| ccagcggggg agtttcataa tgatgcatca aatctacagc accgtcagga ctcgggttta | 420 |
| gaatagtaga aatgatatgt gtacgcacaa tatgtctata tatatgtata atattattca | 480 |
| tatatgtgta tgcataatat gtatatatat aatagtatct taaatgtaat attgaagata | 540 |
| aatagaactt tatatatatt agcgtattag aagtagtata cgtatgaata tagaataaag | 600 |
| aaaaagaaaa taagaaaaga aaggaaaaaa acaaatcagt accggtcggg gagaccaacc | 660 |
| ggcactaatt aggcccttta gtgccctccc gccaccctct cctccctctt ctctcgccgc | 720 |
| cctctcctcc ctctcagctc ttcccgaccc cttcctctcc cactgccgcc ccctccctct | 780 |
| ctccgccgac caccatcgtc ctgcgtgatc tccctctcct caccctcggc tgcccctcct | 840 |
| ctccccttc gctcacccct cactcgtggc agtgaggagc agcggcaaca catagatccg | 900 |
| gtggtggcag tgcaggttcc agtgaagaag gagctagcac ggatccgacg aagaaggagc | 960 |
| tggttgcggt ggcgtaggtg gcggccctg gcggcgcggc ctcagcttcc tctccccgta | 1020 |
| cgcctctctc tctctctctc tatgagccgg atccggtagg accaaggcag ttggcggctg | 1080 |

```
gtggggcggc aacggccaga tccagcgaga tgcggccggt cggatccggc gaggcagcgc    1140
aaggccgggg cgtaaggcgg ccggcagcac cattttttg ttttttaat aggccttcac      1200 cgccagttcc aaaaccagcg gtgatggggt atccccatca ctaccgaaag tcagacgatg    1260
gatccaaacc gacggtgaag actggtttgg agccggcagt gatgaacctc tggagtagtg    1320
cttatggctg ggggcattga cattcttttt actaactttc ttcctaccac gtagtatgca    1380
ataattgtac gtaatactag tagctgatga taagtttgat ataagactat caagcggtct    1440
cgacatttca caatctcgtg cagcacatgg acagctatac taacgagaag tcgaggacga    1500
cagcccaccg acttgacaaa tctgtacaaa atatgctaga aaaatattgc accaatcaaa    1560
cattgcccat caaggccacc aaggatacat gatgacaacg ccaatcaga cttcaaagat     1620 atctcaacat catacacaca gaaggaagag atgatgactc cagtttaact ttcatcgacg    1680
actcctataa atacgaccct cttcctgtac gcctcctcat tccaac                   1726

<210> SEQ ID NO 11
<211> LENGTH: 40
<212> TYPE: DNA
<213> ORGANISM: Setaria italica

<400> SEQUENCE: 11
acaggaacgg gattcttcct tcttctggcc attagctcca                          40

<210> SEQ ID NO 12
<211> LENGTH: 1778
<212> TYPE: DNA
<213> ORGANISM: Setaria italica

<400> SEQUENCE: 12
tggtaaaatc aattcatatg cttatacttc aaaaaccaat ttatgtgtat atacttggaa    60
aaattagatt aagtatttca atttatttgc ttatatttca aaaataaaatt cttgtgcata   120 tacttagaaa aattagatta agtatttcaa tttatttgct tatacttcaa aaatcaattc    180
ttgtgtacat acttagaaaa attagattaa gtatttcaat ttaattgctt atatttgaag    240
taagtcaatt gtgcaaaccc attgatctac tatatatgca ataaactttg ccaatgacac    300
agatgatgta caggaaagat agaatcttca agtggatttc ttctagacga ggtcataaat    360
ccagcggggg agtttcataa tgatgcatca atctacagc accgtcagga ctcgggttta    420
gaatagtaga tatgatatgt gtacgcacaa tatgtctata tatatgtata atattattca    480
tatatgtgta tgcataatat gtatatatat aatagtatct aaatgtaat attgaagata    540 aatagaactt tatatatatt agcgtattag aagtagtata cgtaagaata tagaataaag    600
aaaagaaaat aagaaaagaa aggaaaaaac aaatcagtac cggttgggga gaccaaccgg    660
cactaattag gcccttagt gccttcccgc caccctctcc tccctcttct ctcgccgccc     720
tctcctccct ctcagctcct cccgacccct tcctctccca ctgtcgcccc ctccctctcc   780
ccgccgacca ccatcgtcgt gcgtgatctc cctctcctca ccctcggctg cccctcctct   840
ccccccttcg ctcaccccctc actcgtggca gtgaggagcg gcggcggggt gagagcagcg   900
gcaacacata gatccggtgg tggcggtgca ggttccagtg aagaaggagc tagcacggat    960
ccgacgaaga aggagctggt tgcggtggcg taggtgggcg gccctggcgg cgcggcctca    1020
gcttcctctc cccgtacgcc tctctctctc tctatgagcc ggatccggta ggaccaaggc    1080
agttggcggc tggtggggcg gcaacggcca gatccagcga gatgctgccg gtcggatccg    1140
```

```
gcgaggcagc gcaaggccgg ggcgtaaggc ggccggcagc accattttttt tgttttttta    1200
acaggccttc accgccagtt ccaaaaccag cggtgatggg gtatcccat cactaccgaa     1260
agtcagacga tggatccaaa ccgacggtga agactggttt ggagccggca gtgatgaacc    1320
tctggagtag tgcttatggc tgggggcatt gacattcttt ttactaactt tcttcctacc    1380
acgtagtatg caataattgt acgtaatact agtagctgat gataagtttg atataagact    1440
atcaagcggt ctcgacattt cacaatctcg tgcaacacat ggacagctat actaacgaga    1500
agtcgagaac gacagcccac cgacttgaca aatctgtaca aaatatgcta gaaaatatt     1560
gcaccaatca acattgccc atcaaggcca ccaaggatac atgatgacaa cggccaatca     1620
gacttcaaag atatctcaac atcatacaca cagaaggaag agatgatgac tccagtttaa    1680
ctttcatcga cgactcctat aaatacgacc ctcttcctgt acgcctcctc attccaacac    1740
aggaacggga ttcttccttc ttctggccat tagctcca                            1778

<210> SEQ ID NO 13
<211> LENGTH: 1738
<212> TYPE: DNA
<213> ORGANISM: Setaria italica

<400> SEQUENCE: 13
tggtaaaatc aattcatatg cttatacttc aaaaaccaat ttatgtgtat atacttggaa     60
aaattagatt aagtatttca atttatttgc ttatatttca aaaataaatt cttgtgcata    120
tacttagaaa aattagatta agtatttcaa tttatttgct tatacttcaa aaatcaattc    180
ttgtgtacat acttagaaaa attagattaa gtatttcaat ttaattgctt atatttgaag    240
taagtcaatt gtgcaaaccc attgatctac tatatatgca ataaactttg ccaatgacac    300
agatgatgta caggaaagat agaatcttca agtggatttc ttctagacga ggtcataaat    360
ccagcggggg agtttcataa tgatgcatca aatctacagc accgtcagga ctcgggttta    420
gaatagtaga tatgatatgt gtacgcacaa tatgtctata tatatgtata atattattca    480
tatatgtgta tgcataatat gtatatatat aatagtatct taaatgtaat attgaagata    540
aatagaactt tatatatatt agcgtattag aagtagtata cgtaagaata tagaataaag    600
aaaagaaaat aagaaaagaa aggaaaaaac aaatcagtac cggttgggga gaccaaccgg    660
cactaattag gcccttttagt gccttcccgc caccctctcc tccctcttct ctcgccgccc    720
tctcctccct ctcagctcct cccgacccct tcctctccca ctgtcgcccc ctccctctcc    780
ccgccgacca ccatcgtcgt gcgtgatctc cctctcctca ccctcggctg ccctcctct    840
cccccttcg ctcacccctc actcgtggca gtgaggagcg gcggcggggt gagagcagcg    900
gcaacacata gatccggtgg tggcggtgca ggttccagtg aagaaggagc tagcacggat    960
ccgacgaaga aggagctggt tgcggtggcg taggtgggcg gccctggcgg cgcggcctca   1020
gcttcctctc cccgtacgcc tctctctctc tctatgagcc ggatccggta ggaccaaggc   1080
agttggcggc tggtggggcg gcaacggcca gatccagcga gatgctgccg gtcggatccg   1140
gcgaggcagc gcaaggccgg ggcgtaaggc ggccggcagc accattttttt tgttttttta   1200
acaggccttc accgccagtt ccaaaaccag cggtgatggg gtatcccat cactaccgaa    1260
agtcagacga tggatccaaa ccgacggtga agactggttt ggagccggca gtgatgaacc   1320
tctggagtag tgcttatggc tgggggcatt gacattcttt ttactaactt tcttcctacc   1380
acgtagtatg caataattgt acgtaatact agtagctgat gataagtttg atataagact   1440
atcaagcggt ctcgacattt cacaatctcg tgcaacacat ggacagctat actaacgaga   1500
```

```
agtcgagaac gacagcccac cgacttgaca aatctgtaca aaatatgcta gaaaaatatt   1560
gcaccaatca aacattgccc atcaaggcca ccaaggatac atgatgacaa cggccaatca   1620
gacttcaaag atatctcaac atcatacaca cagaaggaag agatgatgac tccagtttaa   1680 cttttcatcga cgactcctat aaatacgacc ctcttcctgt acgcctcctc attccaac    1738
```

<210> SEQ ID NO 14
<211> LENGTH: 2128
<212> TYPE: DNA
<213> ORGANISM: Setaria italica

<400> SEQUENCE: 14

```
tatcggcgac cgctaagaga agacatttaa aataagtagt cggcattgtg ataaaaagag     60
agcgcgatta ctgatgtgca ggttctcgat tgttgatgaa gtcgactagt cggagtcgat    120
tctgactagt tattgattgt atggaacccg ccctcgacta gttttctagt cgagacgagt    180
agtcgaagta gaccatcctc aactactttt ctagttgaga tgagtagtcg aagtagtcgt    240
cggcgacttg attatttgcc tcaatctgtg tgtgacttga tcgacgagcc gtatgcagca    300
gcttgcggtg gaaaccgact cagtcttcga ttggaacacg gagcgcgtca attctatgtc    360
gacgtagatt tgtctgcttg gaactccaac tcagtgactt gcttcttgtt gagtagattg    420
atcttgatga tgaggtcctt caagctcgcc tgatgatctc gacgatcacc tctacctgac    480
gcgccaactg ttggtgctta gacccagcaa cctaccgagg gggtacccga ggtagtgttt    540
tgtggtgggg ctcgtcgaag atcaggaact tgaaggtgaa ctcgaacaca cgatttagac    600
aagttcgggc tgcttatgcc gcataatacc ccatgtcatg tgtgttggtt ggattgtatt    660
gattgatcag atatttggag ggggccctgc ctcgccttat attgcccatt gccggaggca    720
gggctacagg tcggttgttg tacaagagta ctagtcggtt ttgaccagcg agtcctactc    780
taattgctac aagtagtttc ctaatccttg actagtcctt gtccgccacg tagaccacga    840
cgtcttgcac ctagtctctg tgtttgatac atcttggtgt acagtccgat attgtaggac    900
tatccaagct tcccagtagg cccatagatg tatggccgac aactggataa tgtaactctg    960
ggtcagtact atccttatct atatagacac aaacaacgta ctatagcaga agtttaagct   1020
cgtaacccac caatatttgg tggcatagac cacgtattgc tgatatagtg ctcgtaaccc   1080
accaatattt cgtggcatag agatctctta ggcaataaat tagcagtacg aaacaatcta   1140
tgtccacgtg ttgctaatac aatgttctaa accttacagc ctactggaca gttctctagc   1200
catgatacat gtgcatgtcc gaacaaatat ttatgggtac ccgaaaggtt aattttttgt   1260
agtatttatg aggggagggg gggcgttgac gaaaaaaata acttagctaa gcgtaattgg   1320
cttaaaaaca tacaatgttg ttccagcatc aagcctacgt gatcatttca caaaccaac    1380 tcaaaagata ggtgtcatgt tccttttagt gcaaaactta aggacaccta ccttgcaaaa   1440
cttagctttg ttacccagaa tgaaccgcta agctcgagga gctctgaact tacatgacca   1500
aatatattaa acacaaaagt catgcatgat tttctttaat aagtatcgag caatatggtt   1560
cgggtgtctt tcgtctcata cctctattgt cctccgtgat caacaagggt ggatccgggt   1620
ggtgcaaggg ggctcaagcc cccctacctc tcccaaagga gaaagaaggg agaagaaagt   1680
gaaggaagaa gaaacccccct atattctaat gctacctccg ccactgctga tcaacacaac   1740
attcttaaaa ccatttcctt ggcatttgcg catgttacaa ggtacaaaag agccagccca   1800
tatgccaagt tactaaacta aactatgatc caccatggag cgagaacaaa cgtcaacagg   1860
```

```
catcaaccaa tgcagcaatc ttgatcgcta gtactgtccg gcattatatc tgaaacaaat    1920
ccagatcacc catctcatca cagtcacatg cattcatggt cacgggaacc gttagcaaac    1980
caccaactaa tcagcattgc aacactcttc ctcctataaa tgcagcgagc gggggacacc    2040
ataaaccatc acaggcactt aggatcaagt taattttgtt tctgctttgt gcgcctgtgt    2100
tccagtaatt actttccgtg tagcaaaa                                       2128

<210> SEQ ID NO 15
<211> LENGTH: 2062
<212> TYPE: DNA
<213> ORGANISM: Setaria italica

<400> SEQUENCE: 15
tatcggcgac cgctaagaga agacatttaa aataagtagt cggcattgtg ataaaaagag      60
agcgcgatta ctgatgtgca ggttctcgat tgttgatgaa gtcgactagt cggagtcgat     120
tctgactagt tattgattgt atggaacccg ccctcgacta gttttctagt cgagacgagt     180
agtcgaagta gaccatcctc aactactttt ctagttgaga tgagtagtcg aagtagtcgt     240
cggcgacttg attatttgcc tcaatctgtg tgtgacttga tcgacgagcc gtatgcagca     300
gcttgcggtg gaaaccgact cagtcttcga ttggaacacg gagcgcgtca attctatgtc     360
gacgtagatt tgtctgcttg gaactccaac tcagtgactt gcttcttgtt gagtagattg     420
atcttgatga tgaggtcctt caagctcgcc tgatgatctc gacgatcacc tctacctgac     480
gcgccaactg ttggtgctta gacccagcaa cctaccgagg gggtacccga ggtagtgttt     540
tgtggtgggg ctcgtcgaag atcaggaact tgaaggtgaa ctcgaacaca cgatttagac     600
aagttcgggc tgcttatgcc gcataatacc ccatgtcatg tgtgttggtt ggattgtatt     660
gattgatcag atatttggag ggggccctgc ctcgccttat attgcccatt gccggaggca     720
gggctacagg tcggttgttg tacaagagta ctagtcggtt ttgaccagcg agtcctactc     780
taattgctac aagtagtttc ctaatccttg actagtcctt gtccgccacg tagaccacga     840
cgtcttgcac ctagtctctg tgtttgatac atcttggtgt acagtccgat attgtaggac     900
tatccaagct tcccagtagg cccatagatg tatggccgac aactggataa tgtaactctg     960
ggtcagtact atccttatct atatagacac aaacaacgta ctatagcaga agtttaagct    1020
cgtaacccac caatatttgg tggcatagac acgtattgc tgatatagtg ctcgtaaccc    1080 accaatatttt cgtggcatag agatctctta ggcaataaat tagcagtacg aaacaatcta    1140
tgtccacgtg ttgctaatac aatgttctaa accttacagc ctactggaca gttctctagc    1200
catgatacat gtgcatgtcc gaacaaatat ttatgggtac ccgaaaggtt aatttttttgt    1260 agtatttatg aggggaggg gggcgttgac gaaaaaaata acttagctaa gcgtaattgg    1320
cttaaaaaca tacaatgttg ttccagcatc aagcctacgt gatcatttca caaaaccaac    1380
tcaaaagata ggtgtcatgt tccttttagt gcaaaactta aggacaccta ccttgcaaaa    1440
cttagctttg ttacccagaa tgaaccgcta agctcgagga gctctgaact tacatgacca    1500
aatatattaa acacaaaagt catgcatgat tttctttaat aagtatcgag caatatggtt    1560
cgggtgtctt tcgtctcata cctctattgt cctccgtgat caacaagggt ggatccgggt    1620
ggtgcaaggg ggctcaagcc cccctacctc tcccaaagga gaagaaggg agaagaaagt    1680 gaaggaagaa gaaacccccct atattctaat gctacctccg ccactgctga tcaacacaac    1740
attcttaaaa ccatttcctt ggcatttgcg catgttacaa ggtacaaaag agccagccca    1800
tatgccaagt tactaaacta aactatgatc caccatggag cgagaacaaa cgtcaacagg    1860
```

```
catcaaccaa tgcagcaatc ttgatcgcta gtactgtccg gcattatatc tgaaacaaat    1920
ccagatcacc catctcatca cagtcacatg cattcatggt cacgggaacc gttagcaaac    1980
caccaactaa tcagcattgc aacactcttc ctcctataaa tgcagcgagc gggggacacc    2040
ataaaccatc acaggcactt ag                                             2062

<210> SEQ ID NO 16
<211> LENGTH: 66
<212> TYPE: DNA
<213> ORGANISM: Setaria italica

<400> SEQUENCE: 16
gatcaagtta attttgtttc tgctttgtgc gcctgtgttc cagtaattac tttccgtgta    60
gcaaaa                                                               66

<210> SEQ ID NO 17
<211> LENGTH: 1629
<212> TYPE: DNA
<213> ORGANISM: Setaria italica

<400> SEQUENCE: 17
agacccagca acctaccgag ggggtacccg aggtagtgtt ttgtggtggg gctcgtcgaa    60
gatcaggaac ttgaaggtga actcgaacac acgatttaga caagttcggg ctgcttatgc    120
cgcataatac cccatgtcat gtgtgttggt tggattgtat tgattgatca gatatttgga    180
gggggccctg cctcgcctta tattgcccat tgccggaggc agggctacag gtcggttgtt    240
gtacaagagt actagtcggt tttgaccagc gagtcctact ctaattgcta caagtagttt    300
cctaatcctt gactagtcct tgtccgccac gtagaccacg acgtcttgca cctagtctct    360
gtgtttgata catcttggtg tacagtccga tattgtagga ctatccaagc ttcccagtag    420
gcccatagat gtatggccga caactggata atgtaactct gggtcagtac tatccttatc    480
tatatagaca caaacaacgt actatagcag aagtttaagc tcgtaaccca ccaatatttg    540
gtggcataga ccacgtattg ctgatatagt gctcgtaacc caccaatatt tcgtggcata    600
gagatctctt aggcaataaa ttagcagtac gaaacaatct atgtccacgt gttgctaata    660
caatgttcta aaccttacag cctactggac agttctctag ccatgataca tgtgcatgtc    720
cgaacaaata tttatgggta cccgaaaggt taatttttttg tagtatttat gagggggagg    780
ggggcgttga cgaaaaaaat aacttagcta agcgtaattg gcttaaaaac atacaatgtt    840
gttccagcat caagcctacg tgatcatttc acaaaaccaa ctcaaaagat aggtgtcatg    900
ttccttttag tgcaaaactt aaggacacct accttgcaaa acttagcttt gttacccaga    960
atgaaccgct aagctcgagg agctctgaac ttacatgacc aaatatatta aacacaaaag    1020
tcatgcatga ttttctttaa taagtatcga gcaatatggt tcgggtgtct ttcgtctcat    1080
acctctattg tcctccgtga tcaacaaggg tggatccggg tggtgcaagg gggctcaagc    1140 cccctacct ctcccaaagg agaagaagg gagaagaaag tgaaggaaga agaaaccccc    1200
tatattctaa tgctacctcc gccactgctg atcaacacaa cattcttaaa accatttcct    1260
tggcatttgc gcatgttaca aggtacaaaa gagccagccc atatgccaag ttactaaact    1320
aaactatgat ccaccatgga gcgagaacaa acgtcaacag gcatcaacca atgcagcaat    1380
cttgatcgct agtactgtcc ggcattatat ctgaaacaaa tccagatcac ccatctcatc    1440
acagtcacat gcattcatgg tcacgggaac cgttagcaaa ccaccaacta atcagcattg    1500
```

```
caacactctt cctcctataa atgcagcgag cggggacac cataaaccat cacaggcact      1560
taggatcaag ttaattttgt ttctgctttg tgcgcctgtg ttccagtaat tactttccgt      1620
gtagcaaaa                                                              1629

<210> SEQ ID NO 18
<211> LENGTH: 1563
<212> TYPE: DNA
<213> ORGANISM: Setaria italica

<400> SEQUENCE: 18
agacccagca acctaccgag ggggtacccg aggtagtgtt ttgtggtggg gctcgtcgaa        60
gatcaggaac ttgaaggtga actcgaacac acgatttaga caagttcggg ctgcttatgc       120
cgcataatac cccatgtcat gtgtgttggt tggattgtat tgattgatca gatatttgga       180
gggggccctg cctcgcctta tattgcccat tgccggaggc agggctacag gtcggttgtt       240
gtacaagagt actagtcggt tttgaccagc gagtcctact ctaattgcta caagtagttt       300
cctaatcctt gactagtcct tgtccgccac gtagaccacg acgtcttgca cctagtctct       360
gtgtttgata catcttggtg tacagtccga tattgtagga ctatccaagc ttcccagtag       420
gcccatagat gtatggccga caactggata atgtaactct gggtcagtac tatccttatc       480
tatatagaca caaacaacgt actatagcag aagtttaagc tcgtaaccca ccaatatttg       540
gtggcataga ccacgtattg ctgatatagt gctcgtaacc caccaatatt tcgtggcata       600
gagatctctt aggcaataaa ttagcagtac gaaacaatct atgtccacgt gttgctaata       660
caatgttcta aaccttacag cctactggac agttctctag ccatgataca tgtgcatgtc       720
cgaacaaata tttatgggta cccgaaaggt taattttttg tagtatttat gaggggaggg       780
ggggcgttga cgaaaaaaat aacttagcta agcgtaattg gcttaaaaac atacaatgtt       840
gttccagcat caagcctacg tgatcatttc acaaaaccaa ctcaaaagat aggtgtcatg       900
ttccttttag tgcaaaactt aaggacacct accttgcaaa acttagcttt gttacccaga       960
atgaaccgct aagctcgagg agctctgaac ttacatgacc aaatatatta aacacaaaag      1020
tcatgcatga ttttctttaa taagtatcga gcaatatggt tcgggtgtct ttcgtctcat      1080
acctctattg tcctccgtga tcaacaaggg tggatccggg tggtgcaagg gggctcaagc      1140 cccctacct ctcccaaagg agaaagaagg gagaagaaag tgaaggaaga agaaccccc        1200 tatattctaa tgctacctcc gccactgctg atcaacacaa cattcttaaa accatttcct      1260
tggcatttgc gcatgttaca aggtacaaaa gagccagccc atatgccaag ttactaaact      1320
aaactatgat ccaccatgga gcgagaacaa acgtcaacag gcatcaacca atgcagcaat      1380
cttgatcgct agtactgtcc ggcattatat ctgaaacaaa tccagatcac ccatctcatc      1440
acagtcacat gcattcatgg tcacgggaac cgttagcaaa ccaccaacta atcagcattg      1500
caacactctt cctcctataa atgcagcgag cggggacac cataaaccat cacaggcact      1560
tag                                                                  1563

<210> SEQ ID NO 19
<211> LENGTH: 981
<212> TYPE: DNA
<213> ORGANISM: Setaria italica

<400> SEQUENCE: 19
gtgttgctaa tacaatgttc taaaccttac agcctactgg acagttctct agccatgata        60
catgtgcatg tccgaacaaa tatttatggg tacccgaaag gttaattttt tgtagtattt       120
```

```
atgaggggga gggggcgtt gacgaaaaaa ataacttagc taagcgtaat tggcttaaaa        180
acatacaatg ttgttccagc atcaagccta cgtgatcatt tcacaaaacc aactcaaaag        240
ataggtgtca tgttcctttt agtgcaaaac ttaaggacac ctaccttgca aaacttagct        300
ttgttaccca gaatgaaccg ctaagctcga ggagctctga acttacatga ccaaatatat        360
taaacacaaa agtcatgcat gattttcttt aataagtatc gagcaatatg gttcgggtgt        420
ctttcgtctc atacctctat tgtcctccgt gatcaacaag ggtggatccg ggtggtgcaa        480
gggggctcaa gcccccctac ctctcccaaa ggagaaagaa gggagaagaa agtgaaggaa        540
gaagaaaccc cctatattct aatgctacct ccgccactgc tgatcaacac aacattctta        600
aaaccatttc cttggcattt gcgcatgtta caaggtacaa aagagccagc ccatatgcca        660
agttactaaa ctaaactatg atccaccatg gagcgagaaa aaacgtcaac aggcatcaac        720
caatgcagca atcttgatcg ctagtactgt ccggcattat atctgaaaca aatccagatc        780
acccatctca tcacagtcac atgcattcat ggtcacggga accgttagca aaccaccaac        840
taatcagcat tgcaacactc ttcctcctat aaatgcagcg agcggggac accataaacc         900 atcacaggca cttaggatca agttaatttt gtttctgctt tgtgcgcctg tgttccagta        960
attactttcc gtgtagcaaa a                                                  981
```

<210> SEQ ID NO 20
<211> LENGTH: 915
<212> TYPE: DNA
<213> ORGANISM: Setaria italica
<400> SEQUENCE: 20

```
gtgttgctaa tacaatgttc taaaccttac agcctactgg acagttctct agccatgata         60
catgtgcatg tccgaacaaa tatttatggg tacccgaaag gttaattttt tgtagtattt        120
atgaggggga gggggcgtt gacgaaaaaa ataacttagc taagcgtaat tggcttaaaa        180
acatacaatg ttgttccagc atcaagccta cgtgatcatt tcacaaaacc aactcaaaag        240
ataggtgtca tgttcctttt agtgcaaaac ttaaggacac ctaccttgca aaacttagct        300
ttgttaccca gaatgaaccg ctaagctcga ggagctctga acttacatga ccaaatatat        360
taaacacaaa agtcatgcat gattttcttt aataagtatc gagcaatatg gttcgggtgt        420
ctttcgtctc atacctctat tgtcctccgt gatcaacaag ggtggatccg ggtggtgcaa        480
gggggctcaa gcccccctac ctctcccaaa ggagaaagaa gggagaagaa agtgaaggaa        540
gaagaaaccc cctatattct aatgctacct ccgccactgc tgatcaacac aacattctta        600
aaaccatttc cttggcattt gcgcatgtta caaggtacaa aagagccagc ccatatgcca        660
agttactaaa ctaaactatg atccaccatg gagcgagaaa aaacgtcaac aggcatcaac        720
caatgcagca atcttgatcg ctagtactgt ccggcattat atctgaaaca aatccagatc        780
acccatctca tcacagtcac atgcattcat ggtcacggga accgttagca aaccaccaac        840
taatcagcat tgcaacactc ttcctcctat aaatgcagcg agcggggac accataaacc         900 atcacaggca cttag                                                        915
```